(12) United States Patent
Okada et al.

(10) Patent No.: US 8,623,355 B2
(45) Date of Patent: Jan. 7, 2014

(54) METHODS FOR SUPPRESSING ACUTE REJECTION OF A HEART TRANSPLANT

(75) Inventors: Masaji Okada, Osaka (JP); Masafumi Takahashi, Nagano (JP); Atsushi Izawa, Nagano (JP); Yoshiyuki Ohsugi, Tokyo (JP); Masahiko Mihara, Shizuoka (JP)

(73) Assignees: Chugai Seiyaku Kabushiki Kaisha, Tokyo (JP); National Hospital Organization, Tokyo (JP); Shinshu University, Nagano (JP)

( * ) Notice: Subject to any disclaimer, the term of this patent is extended or adjusted under 35 U.S.C. 154(b) by 0 days.

(21) Appl. No.: 12/085,065

(22) PCT Filed: Nov. 15, 2006

(86) PCT No.: PCT/JP2006/322726
§ 371 (c)(1),
(2), (4) Date: Jun. 1, 2009

(87) PCT Pub. No.: WO2007/058194
PCT Pub. Date: May 24, 2007

(65) Prior Publication Data
US 2009/0263384 A1    Oct. 22, 2009

(30) Foreign Application Priority Data
Nov. 15, 2005  (JP) .................................. 2005-330637
Jun. 21, 2006  (JP) .................................. 2006-170950

(51) Int. Cl.
*A61K 39/395*    (2006.01)
*C07K 16/00*     (2006.01)
*C07K 16/28*     (2006.01)
*A61P 37/06*     (2006.01)

(52) U.S. Cl.
USPC ................ 424/130.1; 424/133.1; 424/141.1; 424/143.1; 530/387.1; 530/387.3; 530/388.1; 530/388.22

(58) Field of Classification Search
None
See application file for complete search history.

(56) References Cited

U.S. PATENT DOCUMENTS

| | | | |
|---|---|---|---|
| 5,216,128 A | 6/1993 | Novick et al. | |
| 5,530,101 A | 6/1996 | Queen et al. | |
| 5,621,077 A | 4/1997 | Novick et al. | |
| 5,639,455 A | 6/1997 | Shimamura et al. | |
| 5,670,373 A | 9/1997 | Kishimoto | |
| 5,795,965 A | 8/1998 | Tsuchiya et al. | |
| 5,817,790 A | 10/1998 | Tsuchiya et al. | |
| 5,856,135 A | 1/1999 | Tsuchiya et al. | |
| 5,888,510 A * | 3/1999 | Kishimoto et al. ........ 424/141.1 |
| 6,074,643 A | 6/2000 | Barbera-Guillem | |
| 6,121,423 A | 9/2000 | Tsuchiya et al. | |
| 6,261,560 B1 | 7/2001 | Tsujinaka et al. | |
| 6,552,083 B1 | 4/2003 | Isobe et al. | |
| 6,723,319 B1 | 4/2004 | Ito et al. | |
| 7,291,721 B2 | 11/2007 | Giles-Komar et al. | |
| 7,320,792 B2 | 1/2008 | Ito et al. | |
| 7,414,024 B2 | 8/2008 | Blay et al. | |
| 7,479,543 B2 | 1/2009 | Tsuchiya et al. | |
| 7,521,052 B2 | 4/2009 | Okuda et al. | |
| 7,781,617 B2 | 8/2010 | Koudou et al. | |
| 7,824,674 B2 | 11/2010 | Ito et al. | |
| 8,226,611 B2 | 7/2012 | Chen et al. | |
| 8,470,316 B2 | 6/2013 | Yasunami | |
| 2001/0001663 A1 | 5/2001 | Kishimoto et al. | |
| 2002/0119150 A1* | 8/2002 | Kirk et al. ................. 424/144.1 |
| 2004/0170626 A1 | 9/2004 | Schuurman et al. | |
| 2005/0096257 A1 | 5/2005 | Shima et al. | |
| 2005/0142635 A1 | 6/2005 | Tsuchiya et al. | |
| 2005/0158317 A1 | 7/2005 | Blay et al. | |
| 2006/0039902 A1 | 2/2006 | Young et al. | |
| 2006/0111316 A1 | 5/2006 | Lawless | |
| 2006/0165696 A1 | 7/2006 | Okano et al. | |
| 2006/0188502 A1 | 8/2006 | Giles-Komar et al. | |
| 2006/0193772 A1 | 8/2006 | Ochiai et al. | |
| 2006/0251653 A1 | 11/2006 | Okuda et al. | |
| 2006/0292147 A1 | 12/2006 | Yoshizaki et al. | |
| 2007/0036785 A1 | 2/2007 | Kishimoto et al. | |
| 2007/0134242 A1 | 6/2007 | Nishimoto et al. | |

(Continued)

FOREIGN PATENT DOCUMENTS

| | | |
|---|---|---|
| CN | 1164194 | 11/1997 |
| CN | 1297357 | 5/2001 |

(Continued)

OTHER PUBLICATIONS

Quentmeier et al, The Journal of Immunology, 1992, vol. 149, No. 10, pp. 3316-3320.*

(Continued)

*Primary Examiner* — Bridget E Bunner
*Assistant Examiner* — Fozia Hamud
(74) *Attorney, Agent, or Firm* — Fish & Richardson P.C.

(57) ABSTRACT

The effect of anti-IL-6 receptor antibodies in suppressing cytotoxic T cell induction was examined. The results showed that CTL activity against alloantigens was statistically significantly reduced in mice treated with anti-IL-6 receptor antibodies as compared to mice not treated with antibodies and mice treated with a control antibody. The anti-IL-6 receptor antibody was also administered to recipients of a mouse model for allogenic heart transplantation. As a result, histopathological findings showed that inflammatory cell infiltration into transplanted hearts was suppressed and the survival period of transplanted hearts was significantly prolonged. Thus, the present inventors for the first time discovered that administration of anti-IL-6 receptor antibodies could suppress cytotoxic T cell induction and thereby suppress acute rejection after transplantation.

20 Claims, 7 Drawing Sheets

(56) References Cited

U.S. PATENT DOCUMENTS

| | | | |
|---|---|---|---|
| 2007/0167425 A1* | 7/2007 | Nakade et al. | 514/210.17 |
| 2008/0081041 A1 | 4/2008 | Nemeth | |
| 2009/0022719 A1 | 1/2009 | Mihara et al. | |
| 2009/0022726 A1 | 1/2009 | Zaki et al. | |
| 2009/0220499 A1 | 9/2009 | Yasunami | |
| 2009/0220500 A1 | 9/2009 | Kobara | |
| 2009/0269335 A1 | 10/2009 | Nakashima et al. | |
| 2010/0008907 A1 | 1/2010 | Nishimoto et al. | |
| 2010/0034811 A1 | 2/2010 | Ishida | |
| 2010/0061986 A1 | 3/2010 | Takahashi et al. | |
| 2010/0298542 A1 | 11/2010 | Igawa et al. | |
| 2011/0098450 A1 | 4/2011 | Igawa et al. | |
| 2011/0111406 A1 | 5/2011 | Igawa et al. | |
| 2011/0150869 A1 | 6/2011 | Mitsunaga et al. | |
| 2011/0245473 A1 | 10/2011 | Igawa et al. | |
| 2012/0045453 A1 | 2/2012 | Chen et al. | |
| 2012/0183539 A1 | 7/2012 | Maeda | |

FOREIGN PATENT DOCUMENTS

| | | |
|---|---|---|
| CN | 1694894 | 11/2005 |
| EP | 0721783 A1 | 7/1996 |
| EP | 0791359 A1 | 8/1997 |
| EP | 0 811 384 | 12/1997 |
| EP | 0931544 A2 | 7/1999 |
| EP | 1 108 435 | 6/2001 |
| EP | 1108435 | 6/2001 |
| EP | 1197210 | 4/2002 |
| EP | 1 562 968 | 5/2004 |
| EP | 1 690 550 | 8/2006 |
| EP | 1 707 215 | 10/2006 |
| EP | 1 941 907 | 7/2008 |
| EP | 1 967 207 | 9/2008 |
| EP | 1967209 | 9/2008 |
| EP | 1990060 | 11/2008 |
| EP | 2025346 | 2/2009 |
| ES | 2276525 | 6/2007 |
| FR | 2 694 767 | 2/1994 |
| JP | 6-237772 | 8/1994 |
| JP | 07-046998 | 2/1995 |
| JP | 08-208514 | 8/1996 |
| JP | 2005-524606 | 8/2005 |
| JP | 2005281235 | 10/2005 |
| JP | 2006524685 | 11/2006 |
| JP | 2007-528691 | 10/2007 |
| JP | 2008-37875 | 2/2008 |
| JP | 2008-37876 | 2/2008 |
| JP | 2008-538931 | 11/2008 |
| RU | 2127117 | 3/1999 |
| RU | 2430111 | 9/2011 |
| WO | WO 92/19759 | 11/1992 |
| WO | WO9420488 A1 | 9/1994 |
| WO | WO 94/28159 | 12/1994 |
| WO | WO 95/09873 | 4/1995 |
| WO | WO 96/25174 | 8/1996 |
| WO | 98/36061 | 8/1998 |
| WO | WO 00/10607 | 3/2000 |
| WO | WO0105394 | 1/2001 |
| WO | WO0145678 | 6/2001 |
| WO | WO03105861 A1 | 12/2003 |
| WO | WO2004007701 A1 | 1/2004 |
| WO | WO 2004/039826 | 5/2004 |
| WO | WO2004045507 A2 | 6/2004 |
| WO | WO2004045512 A2 | 6/2004 |
| WO | WO2004071404 A2 | 8/2004 |
| WO | 20040073741 A1 | 9/2004 |
| WO | WO 2004/096273 | 11/2004 |
| WO | WO 2005/028514 | 3/2005 |
| WO | WO 2005/037315 | 4/2005 |
| WO | WO2005044848 A1 | 5/2005 |
| WO | WO 2005/061000 | 7/2005 |
| WO | WO2005107800 A1 | 11/2005 |
| WO | WO 2006/009092 | 1/2006 |
| WO | WO 2006/070286 | 7/2006 |
| WO | WO 2006/119115 | 11/2006 |
| WO | WO 2007/043641 | 4/2007 |
| WO | WO2007046489 | 4/2007 |
| WO | WO2007058194 | 5/2007 |
| WO | WO2007061029 | 5/2007 |
| WO | WO 2007/067976 | 6/2007 |
| WO | WO 2007/076927 | 7/2007 |
| WO | WO2007086490 | 8/2007 |
| WO | WO2007116962 | 10/2007 |
| WO | WO 2008/020079 | 2/2008 |
| WO | WO2008090901 A1 | 7/2008 |
| WO | WO 2009/010539 | 1/2009 |
| WO | WO 2009/041613 | 4/2009 |
| WO | WO 2009/041621 | 4/2009 |
| WO | WO 2009/125825 | 10/2009 |
| WO | WO 2009/148148 | 12/2009 |

OTHER PUBLICATIONS

Jeron et al., "Systemic Immunosuppression Fails to Suppress Cardiac Cytokine induction in Pressure Overload Hypertrophy in Rats," Immunobiology, 205(1):51-60 (2002).

Kobara et al., "Inhibition of interleukin-6 signaling attenuates left ventricular remodeling after myocardial infarction in mice," Journal of the American Heart Association, 112(17):851 (2005).

Kurdi et al., "Increased expression of IL-6 and LIF in the hypertrophied left ventricle of TGR(mRen2)27 and SHR rats," Molecular and Cellular Biochemistry, 269(1):95-101 (2005).

Okamoto et al., "Inhibition of Interleukin-6 Signaling Attenuates Left Ventricular Remodeling After Experimental Myocardial Infarction," Journal of Cardiac Failure, 11(9): P066 (2005).

European Search Report for App. Ser. No. EP 06 81 2073, dated Nov. 20, 2009, 6 pages.

Ford et al., "Evidence that Production of Interleukin 6 within the Rejecting Allograft Coincides with Cytotoxic T Lymphocyte Development," Transplantation, 51(3):656-661 (1991).

Luo et al., "A Proteasome Inhibitor Effectively Prevents Mouse Heart Allograft Rejection," Transplantation, 72(2):196-202 (2001).

European Search Report for App. Ser. No. EP 06 83 2657, dated Nov. 25, 2009, 5 pages.

Biswas et al., "Involvement of IL-6 in the paracrine production of VEGF in ocular HSV-1 infection," Exp. Eye Res., 82(1):46-54 (2006).

Giugliano et al., "Verapamil inhibits interleukin-6 and vascular endothelial growth factor production in primary cultures of keloid fibroblasts," Br. J. Plast. Surg., 56(8):804-809 (2003).

Hoffman et al., "Inhibitory effects of verapamil isomers on the proliferation of choroidal endothelial cells," Graefe's Arch. Clin. Exp. Ophthalmol., 244(3):376-381 (2006).

Park et al., "Interleukin-6 protects MIN6 beta cells from cytokine-induced apoptosis," Ann. N.Y. Acad. Sci., 1005:242-249 (2003).

European Search Report for App. Ser. No. EP 06 81 1729, dated Nov. 17, 2009, 5 pages.

USPTO Restriction Requirement in U.S. Appl. No. 12/090,676, dated Mar. 12, 2010, 4 pages.

European Search Report for App. Ser. No. 07 70 7458, dated Nov. 30, 2009, 5 pages.

U.S. Appl. No. 12/094,644, filed Feb. 27, 2009, Nakashima et al.
U.S. Appl. No. 12/161,733, filed Jul. 22, 2008, Ishida.
U.S. Appl. No. 12/296,193, filed Oct. 6, 2008, Nishimoto et al.

Akira et al., "Interleukin-6 in biology and medicine," Adv. Immunol., 54:1-78 (1993).

Alvarez et al., "Tumor necrosis factor-α exerts interleukin-6-dependent and -independent effects on cultured skeletal muscle cells," Biochim. Biophys. Acta, 1542:66-72 (2002).

Barton-Davis et al., "Viral mediated expression of insulin-like growth factor I blocks the aging-related loss of skeletal muscle function," Proc. Natl. Acad. Sci. USA, 95:15603-07 (1998).

Benda et al., "Interleukin-6 in islet xenograft rejection," Transplant Int., 14:63-71 (2001).

Bogdanovich et al., "Functional improvement of dystrophic muscle by myostatin blockade," Nature, 420:418-421 (2002).

(56) References Cited

OTHER PUBLICATIONS

Campbell et al., "Essential role for interferon-γ and interleukin-6 in autoimmune insulin-dependent diabetes in NOD/Wehi mice," *J. Clin. Invest.*, 87:739-742 (1991).
Campbell et al., "Evidence for IL-6 production by and effects on the pancreatic β-cell," *J. Immunol.*, 143:1188-91 (1989).
Choi et al., "IL-6 protects pancreatic islet beta cells from pro-inflammatory cytokines-induced cell death and functional impairment in vitro and in vivo," *Transpl. Immunol.*, 13:43-53 (2004).
Dangott et al., "Dietary creatine monohydrate supplementation increases satellite cell mitotic activity during compensatory hypertrophy," *Int. J. Sports Med.*, 21:13-16 (2000).
Darr and Schultz, "Hindlimb suspension suppresses muscle growth and satellite cell proliferation," *J. Appl. Physiol.*, 67:1827-34 (1989).
Ding et al., "The change of plasma interleukin-6 level and cardiac protective effect of monoclonal antibody to IL-6 during myocardial infarction reperfusion," *Chin. J. Cardiol.*, 27:29-32 (1999) (with English Abstract).
Finkel et al., "Negative inotropic effects of cytokines on the heart mediated by nitric oxide," *Science*, 257:387-389 (1992).
Fredj et al., "Role of interleukin-6 in cardiomyocyte/cardiac fibroblast interactions during myocyte hypertrophy and fibroblast proliferation," *J. Cell. Physiol.*, 204:428-436 (2005).
Fuchs et al., "Role of interleukin-6 for LV remodeling and survival after experimental myocardial infarction," *FASEB J.*, 17: 2118-20 (2003).
Garry et al., "Myogenic stem cell function is impaired in mice lacking the *forkhead*/winged helix protein MNF," *Proc. Natl. Acad. Sci. USA*, 97:5416-21 (2000).
Garry et al., "Persistent expression of MNF identifies myogenic stem cells in postnatal muscles," *Dev. Biol.*, 188:280-294 (1997).
Grossniklaus and Green, "Choroidal neovascularization," *Am. J. Ophthalmol.*, 137:496-503 (2004).
Gwechengerger et al., "Cardiac myocytes produce interleukin-6 in culture and in viable border zone of reperfused infarctions," *Circulation*, 99:546-551 (1999).
Hirano et al., "Complementary DNA for a novel human interleukin (BSF-2) that induces B lymphocytes to produce immunoglobulin," *Nature*, 324:73-76 (1986).
Hirata et al., "Characterization of IL-6 receptor expression by monoclonal and polyclonal antibodies," *J. Immunol.*, 143:2900-06 (1989).
Hirota et al., "Continuous activation of gp130, a signal-transducing receptor component for interleukin 6-related cytokines, causes myocardial hypertrophy in mice," *Proc. Natl. Acad. Sci. USA*, 92:4862-66 (1995).
Horinaga et al., "Clinical and pathologic significance of activation of signal transducer and activator of transcription 3 in prostate cancer," *Urology*, 66:671-675 (2005).
Huang and Vietta "A monoclonal anti-human IL-6 receptor antibody inhibits the proliferation of human myeloma cells," *Hybridoma*, 12:621-630 (1993).
Ito et al., *Journal of Japan Surgical Society 107* (special extra issue 2):387, PS-014-5 (2006) (English translation included).
Itoh et al., "Anti-IL-6 receptor antibody down-regulates pro-inflammation cytokine production of Gr-1*CD11b* cells and prevents early loss of islet grafts in the liver of mice in association with engraftments," Transplantation 82(Supp. 3), World Transplant Congress 2006, Abstract No. 2838.
Jejurikar et al., "Skeletal muscle denervation increases satellite cell susceptibility to apoptosis," *Plast. Reconstr. Surg.*, 110:160-168 (2002).
Kami et al., "Gene expression of receptors for IL-6, LIF, and CNTF in regenerating skeletal muscles," *J. Histochem. Cytochem.*, 48:1203-13 (2000).
Kurek et al., "Up-regulation of leukaemia inhibitory factor and interleukin-6 in transected sciatic nerve and muscle following denervation," *Neuromuscul. Disord.*, 6:105-114 (1996).

Kuroda et al., "Prevention of cancer cachexia by a novel nuclear factor κB inhibitor in prostate cancer," *Clin. Cancer Res.*, 11:5590-94 (2005).
Lotz et al., "B cell stimulating factor 2 / interleukin 6 is a costimulant for human thymocytes and T lymphocytes," *J. Exp. Med.*, 167:1253-58 (1988).
Mauro, "Satellite cell of skeletal muscle fibers," *J. Biophys. Biochem. Cytol.*, 9:493-495 (1961).
McCormick and Schultz, "Role of satellite cells in altering myosin expression during avian skeletal muscle hypertrophy," *Dev. Dyn.*, 199:52-63 (1994).
Moss and Leblond, "Satellite cells as the source of nuclei in muscles of growing rats," *Anat. Rec.*, 170:421-435 (1971).
Mozdziak et al., "Hindlimb suspension reduces muscle regeneration," *Eur. J. Appl. Physiol.*, 78:136-140 (1998).
Mozdziak et al., "Muscle regeneration during hindlimb unloading results in a reduction in muscle size after reloading," *J. Appl. Physiol.*, 91:183-190 (2001).
Mozdziak et al., "Quantitation of satellite cell proliferation in vivo using image analysis," *Biotech. Histochem.*, 69:249-252 (1994).
Mozdziak et al., "Unloading of juvenile muscle results in a reduced muscle size 9 wk after reloading," *J. Appl. Physiol.*, 88:158-164 (2000).
Murphy, "The effect of mechanical stretch on proliferation and differentiation of C2C12 cells," *FASEB J.*, 18:A743 (Abstract #476.6) (2004).
Nagai et al., Ensho-Saisei (Inflammation and Regeneration), Jul. 2006; 26(4):367 (#90) (English translation included).
Nakashima et al., "Serum interleukin 6 as a prognostic factor in patients with prostate cancer," *Clin. Cancer Res.*, 6:2702-06 (2000).
Negoro et al., "Activation of JAK/STAT pathway transduces cytoprotective signal in rat acute myocardial infarction," *Cardiovas. Res.*, 47:797-805 (2000).
Nishimoto and Kishimoto, "Inhibition of IL-6 for the treatment of inflammatory diseases," *Curr. Opin. Pharmacol.*, 4:386-391 (2004).
Novick et al., "Monoclonal antibodies to the soluble human IL-6 receptor: affinity purification, ELISA, and inhibition of ligand binding," *Hybridoma*, 10:137-146 (1991).
Okamoto et al., "Interleukin-6 as a paracrine and autocrine growth factor in human prostatic carcinoma cells in vitro," Cancer Res., 57:141-146 (1997).
Okazaki et al., "Characterization of anti-mouse interleukin-6 receptor antibody," *Immunol. Lett.*, 84:231-240 (2002).
Ono et al., "Cytokine gene expression after myocardial infarction in rat hearts," *Circulation*, 98:149-156 (1998).
Pauleikhoff, "Neovascular age-related macular degeneration," *Retina*, 25:1065-84 (2005).
Schultz et al., "Response of satellite cells to focal skeletal muscle injury," *Muscle Nerve*, 8:217-222 (1985).
Schultz, "Acute effects of hindlimb unweighting on satellite cells of growing skeletal muscle," *J. Appl. Physiol.*, 76:266-270 (1994).
Schultz, "Satellite cell proliferative compartments in growing skeletal muscles," *Dev. Biol.*, 175:84-94 (1996).
Seddon et al., "Progression of age-related macular degeneration," *Arch. Ophthalmol.*, 123:774-782 (2005).
Shimazaki et al., "Hito Kotsuzuishu Model to Ko hito IL-6 Juyotai Kotai no Ko Shuyo Koka," *Rinsho Ketsueki*, 38:281-284 (1997) (English translation provided).
Smith et al., "Anti-interleukin-6 monoclonal antibody induces regression of human prostate cancer xenografts in nude mice," *Prostate*, 48:47-53 (2001).
Snow, "Myogenic cell formation in regenerating rat skeletal muscle injured by mincing," *Anat. Rec.*, 188:181-199 (1977).
Snow, "Satellite cell response in rat soleus muscle undergoing hypertrophy due to surgical ablation of synergists," *Anat. Rec.*, 227:437-446 (1990).
Taga et al, "Interleukin-6 triggers the association of its receptor with a possible signal transducer, gp130," *Cell*, 58:573-581 (1989).
Taga et al., "Receptors for B cell stimulatory factor 2," *J Exp. Med.*, 166:967-981 (1987).
Tsujinaka et al., "Interleukin 6 receptor antibody inhibits muscle atrophy and modulates proteolytic systems in interleukin 6 transgenic mice," *J. Clin. Invest.*, 97:244-249 (1996).

(56) References Cited

OTHER PUBLICATIONS

Wang et al., "Mechanical load-dependent regulation of satellite cell and fiber size in rat soleus muscle," Am. J Physiol. Cell. Physiol., 290:C981-C989 (2006).
Warren et al., "Physiological role of tumor necrosis factor I in traumatic muscle injury," FASEB J., 16:1630-32 (2002).
Yamasaki et al., "Cloning and expression of the human interleukin-6 (BSF-2/IFNβ 2) receptor," Science, 241:825-828 (1988).
Yamauchi-Takihara et al., "Hypoxic stress induces cardiac myocyte-derived interleukin-6," Circulation, 91:1520-24 (1995).
Yue et al., "Cytokine expression increases in nonmyocytes from rats with postinfarction heart failure," Am. J. Physiol., 275:H250-H258 (1998).
Zaki et al., "CNTO 328, a Monoclonal Antibody to IL-6, Inhibits Human Tumor-Induced Cachexia in Nude Mice," Int. J. Cancer, 111:592-595 (2004).
International Preliminary Report on Patentability for App. Ser. No. PCT/JP2006/320441, dated Apr. 16, 2008, 5 pages.
Japanese Patent Office, International Search Report for App. Ser. No. PCT/JP2006/320441, mailed Dec. 19, 2006, 2 pages.
International Preliminary Report on Patentability for App. Ser. No. PCT/JP2006/320905, dated Apr. 22, 2008, 8 pages.
Japanese Patent Office, International Search Report for App. Ser. No. PCT/JP2006/320905, mailed Jan. 16, 2007, 2 pages.
International Preliminary Report on Patentability for App. Ser. No. PCT/JP2006/322726, dated May 20, 2008, 9 pages.
Japanese Patent Office, International Search Report for App. Ser. No. PCT/JP2006/322726, mailed Jan. 19, 2007, 5 pages.
International Preliminary Report on Patentability for App. Ser. No. PCT/JP2006/323392, dated May 27, 2008, 9 pages.
Japanese Patent Office, International Search Report for App. Ser. No. PCT/JP2006/323392, mailed Jan. 9, 2007, 4 pages.
International Preliminary Report on Patentability for App. Ser. No. PCT/JP2007/051226, dated Jul. 29, 2008, 6 pages.
Japanese Patent Office, International Search Report for App. Ser. No. PCT/JP2007/051226, mailed May 1, 2007, 2 pages.
International Preliminary Report on Patentability for App. Ser. No. PCT/JP2007/057745, dated Nov. 17, 2008, 6 pages.
Japanese Patent Office, International Search Report for App. Ser. No. PCT/JP2007/057745, mailed Jul. 10, 2007, 2 pages.
Furukawa et al., "Cytokine gene expression during the development of graft coronary artery disease in mice," Jpn.Cir. J., 63:775-782 (1999).
Hornick et al., "Chronic rejection in the heart," Methods Mol. Biol., 333:131-144 (2006).
Izawa et al., "Critical Role of Interleukin-6 and its Crosstalk with AT1R Signaling in Acute Rejection of Murine Cardiac Allografts," Circulation Journal, 71 (Suppl. 1):392 (#PE-269), Annual Scientific Meeting of the Japanese Circulation Society, Kobe, Japan (2007).
Izawa et al., "Interleukin-6 Blockade Attenuates the Development of Both Acute and Chronic Rejection of Murine Cardiac Allografts: A Potential Crosstalk between Interleukin-6 and Signaling through Angiotensin II Type 1 Receptor," American Journal of Transplantation, 7 (Suppl. 11):426 (#1084), American Transplant Congress, San Francisco, CA (2007).
Kurek et al., "The Role of Leukemia Inhibitory Factor in Skeletal Muscle Regeneration," Muscle Nerve, 20:815-822 (1997).
Ramzy et al., "Cardiac allograft vasculopathy: a review," Can. J. Surg., 48:319-327 (2005).
Valantine, "Cardiac allograft vasculopathy after heart transplantation: risk factors and management," J. Heart Lung Transplant., 23(5 Suppl.):S187-S193 (2004).
Webber et al., "Heart and lung transplantation in children," Lancet, 368:53-69 (2006).
Wong et al., "Progress in heart transplantation," Cardiovasc. Pathol., 14:176-180 (2005).
International Search Report for App. U.S. Appl. No. PCT/JP2008/050842, mailed on Feb. 19, 2008, 2 pages.
Bellomo, "The Cytokine Network in the Critically Ill," Anaesth. Intensive Care, 20(3):288-302 (1992).
USPTO Restriction Requirement in U.S. App. No. 12/090,061, dated Aug. 27, 2010, 5 pages.
Shimizu et al., "Cancer anti-angiogenic therapy," Biol. Pharm. Bull., 27(5):599-605 (2004).
Stan et al., "In vivo inhibition of angiogenesis and growth of the human U-87 malignant glial tumor by treatment with an antibody against basic fibroblast growth factor," J. Neurosurg., 82(6):1044-52 (1995).
Tobe et al., "Targeted disruption of the FGF2 gene does not prevent choroidal neovascularization in a murine model," Am. J. Pathol., 153(5):1641-6 (1998).
Fish & Richardson P.C., Response to Restriction Requirement dated Mar. 12, 2010 in U.S. Appl. No. 12/090,676, filed Aug. 31, 2010, 1 page.
Guice et al., "Anti-tumor necrosis factor antibody augments edema formation in caerulein-induced acute pancreatitis," J. Surg. Res., 51(6):495-9 (1991).
Hocking et al., "Mechanisms of pulmonary edema induced by tumor necrosis factor-alpha," Circ. Res., 67(1):68-77 (1990).
Knulst et al., "Cytokine detection and modulation in acute graft vs. host disease in mice," Mediators Inflamm., 3(1):33-40 (1994).
Mukaida et al., rinsho kensa, 35(5):447-452 (1991).
Murata et al., The Saishin-nigaku, 47(11):49-56 (1992).
Ulich et al., "Intratracheal injection of endotoxin and cytokines. II. Interleukin-6 and transforming growth factor beta inhibit acute inflammation," Am. J. Pathol., 138(5):1097-1101 (1991).
Bork, "Powers and pitfalls in sequence analysis: the 70% hurdle," Genome Res., 10:398-400 (2000).
Brenner, "Errors in genome annotation," Trends Genet., 15(4):132-133 (1999).
Doerks et al., "Protein annotation: detective work for function prediction," Trends Genet., 14(6):248-250 (1998).
Kobara et al., "Antibody against interleukin-6 receptor attenuates left ventricular remodelling after myocardial infarction in n. mice," Cardiovasc. Res., 87:424-430 (2010).
Matsushita et al., "Interleukin-6/soluble interleukin-6 receptor complex reduces infarct size via inhibiting myocardial apoptosis," Lab. Invest, 85:1210-1223 (2005).
Ngo et al., "The Protein Folding Problem and Tertiary Structure Prediction, Chapter 14: Computational Complexity Protein Structure Prediction, and the Levinthal Paradox," 433-440 and 492-495 (1994).
Phillips, "The challenge of gene therapy and DNA delivery," J. Pharm. Pharmacol., 53:1169-1174 (2001).
Pirollo et al., "Targeted delivery of small interfering RNA: approaching effective cancer therapies," Cancer Res., 68(5):1247-1250 (2008).
Skolnick et al., "From genes to protein structure and function: novel applications of computational approaches in the genomic era," Trends Biotechnol., 18(1):34-39 (2000).
Vidal et al., "Making sense of antisense," Eur. J. Cancer, 41:2812-2818 (2005).
Wells, "Additivity of mutational effects in proteins," Biochemistry, 29(37):8509-8517 (1990).
USPTO Non-Final Office Action in U.S. App. No. 12/090,676, dated Oct. 6, 2010, 18 pages.
USPTO Restriction Requirement in U.S. Appl. No. 12/296,193, dated Oct. 5, 2010, 6 pages.
Smith et al., "The challenges of genome sequence annotation or 'The devil is in the details,'" Nat. Biotechnol., 15:1222-1223 (1997).
Borsellino et al., "Blocking signaling through the Gp130 receptor chain by interleukin-6 and oncostatin M inhibits PC-3 cell growth and sensitizes the tumor cells to etoposide and cisplatin-mediated cytotoxicity," Cancer, 85:134-44 (1999).
Culig et al., "Interleukin-6 regulates androgen receptor activity and prostate cancer cell growth," Mol. Cell. Endocrinol., 197:231-238 (2002).
Davies et al, "The HGF/SF antagonist NK4 reverses fibroblast- and HGF-induced prostate tumor growth and angiogenesis in vivo," Int. J. Cancer, 106:348-354 (2003).
Eder et al., "Targeting the androgen receptor in hormone-refractory prostate cancer—new concepts," Future Oncol., 1:93-101 (2005).

(56) References Cited

OTHER PUBLICATIONS

Lee et al., "Interleukin-6 protects LNCaP cells from apoptosis induced by androgen deprivation through the Stat3 pathway," Prostate, 60:178-186 (2004).
Paule, "Reappraisal of the concept of hormone therapy in metastatic prostate cancer and implications for treatment," Eur. Urol., 47:729-735 (2005).
Trikha et al., "Targeted anti-interleukin-6 monoclonal antibody therapy for cancer: a review of the rationale and clinical evidence," Clin. Cancer Res., 9:4653-65 (2003).
Xing et al., "The effect of interleukin-6 on the proliferation of prostate cancer cells in vitro and the modulation of this procedure," J. Tongji Med. Univ., 21:225-227 (2001).
European Search Report for App. Ser. No. 06 83 3196, dated Aug. 27, 2009, 5 pages.
Akira et al., "Interleukin-6 in biology and medicine", Advances in Immunology 54:1-78, 1993.
Bertagnolli et al., "IL-4-supported induction of cytolytic T lymphocytes requires IL-2 and IL-6", Cellular Immunology 133(2):327-341, 1991.
Borg et al., "15-deoxyspergualin inhibits interleukin 6 production in in vitro stimulated human lymphocytes", Transplant Immunology 4(2):133-143, 1996.
Fraunberger et al., "Cytokine and cytokine-receptor profiles after liver and heart transplantation", Transplantation Proceedings 27(3):2023-2027, 1995.
Hirano et al., "Complementary DNA for a novel human interleukin (BSF-2) that induces B lymphocytes to produce immunoglobulin", Nature 324(6092):73-76, 1986.
Hirata et al., "Characterization of IL-6 receptor expression by monoclonal and polyclonal antibodies", Journal of Immunology 143(9):2900-2906, 1989.
Huang et al., "A monoclonal anti-human IL-6 receptor antibody inhibits the proliferation of human myeloma cells", Hybridoma 12(5):621-630, 1993.
Kanda et al., "Interleukin-6 and cardiovascular diseases", Jpn. Heart J. 45(2):183-193, 2004.
Kitahara et al., "In vivo anti-tumor effect of human recombinant interleukin-6", Jpn. J. Cancer Res. 81(10):1032-1038, 1990.
Lotz et al., "B cell stimulating factor 2/interleukin 6 is a costimulant for human thymocytes and T lymphocytes", J. Exp. Med. 167(3):1253-1258, 1988.
Ming et al., "IL-6 enhances the generation of cytolytic T lymphocytes in the allogeneic mixed leucocyte reaction", Clin. Exp. Immunol. 89(1):148-153, 1992.
Novick et al., "Monoclonal antibodies to the soluble human IL-6 receptor: affinity purification, ELISA, and inhibition of ligand binding", Hybridoma 10(1):137-146, 1991.
Okada et al., "IL-6/BSF-2 functions as a killer helper factor in the in vitro induction of cytotoxic T cells", Journal of Immunology 141(5):1543-1549, 1988.
Taga et al, "Interleukin-6 triggers the association of its receptor with a possible signal transducer, gp130", Cell 58(3):573-581, 1989.
Taga et al., "Receptors for B cell stimulatory factor 2", J. Exp. Med. 166(4):967-981, 1987.
Tamura et al., "Soluble interleukin-6 receptor triggers osteoclast formation by interleukin 6", Proc. Natl. Acad. Sci. USA 90(24):11924-11928, 1993.
Weyand et al., "Serial interleukin-6 blood levels early after cardiac transplantation", Transplantation Proceedings 24(6):2546, 1992.
Yamasaki et al., "Cloning and expression of the human interleukin-6 (BSF-2/IFNβ 2) receptor", Science 241(4867):825-828, 1988.
Fisniku et al., "Protective effects of PG490-88 on chronic allograft rejection by changing intragraft gene expression profiles," Transplant Proc., 37:1962-1964 (2005).
Kallen et al., "New developments in IL-6 dependent biology and therapy: where do we stand and what are the options?," Expert Opin. Investig. Drugs, 8(9):1327-49 (1999).

Matsuda et al., "Establishment of an interleukin 6 (IL 6)/B cell stimulatory factor 2-dependent cell line and preparation of anti-IL 6 monoclonal antibodies," Eur. J. Immunol., 18:951-956 (1988).
Shimizu et al., "KRP-203, a novel synthetic immunosuppressant, prolongs graft survival and attenuates chronic rejection in rat skin and heart allografts," Circulation, 111:222-229 (2005).
Tamura et al., "Soluble interleukin-6 receptor triggers osteoclast formation by interleukin 6," Proc. Natl. Acad. Sci. U.S.A., 90:11924-11928 (1993).
Fish & Richardson P.C., Response to Species Election Requirement dated Feb. 2, 2011 in U.S. Appl. No. 12/094,644, filed Jul. 25, 2011, 2 pages.
USPTO Final Office Action in U.S. Appl. No. 12/296,193, dated Jul. 26, 2011, 20 pages.
Paul, W.E. (Ed.), Fundamental Immunology, $3^{rd}$ ed., New York: Raven Press, 1993, p. 1124-1125.
USPTO Restriction Requirement in U.S. Appl. No. 12/161,733, dated Jan. 13, 2011, 7 pages.
Klarquist Sparkman, LLP Response to Restriction Requirement dated Oct. 5, 2010 in U.S. Appl. No. 12/296,193, filed Nov. 2, 2010, 2 pages.
USPTO Non-Final Office Action in U.S. Appl. No. 12/296,193, dated Dec. 20, 2010, 12 pages.
Fish & Richardson P.C., Response to Restriction Requirement dated Aug. 27, 2010 in U.S. Appl. No. 12/090,061, filed Feb. 24, 2011, 1 page.
USPTO Non-Final Office Action in U.S. Appl. No. 12/090,061, dated May 3, 2011, 12 pages.
Fish & Richardson P.C., Amendment in Reply to Action dated Oct. 6, 2010, in U.S. Appl. No. 12/090,676, filed Apr. 5, 2011, 12 pages.
Wilansky, "Echocardiography in the Assessment of Complications of Myocardial Infarction," *Texas Heart Institute Journal*, 18:237-242 (1991).
USPTO Final Office Action in U.S. Appl. No. 12/090,676, dated Jun. 8, 2011, 14 pages.
Fish & Richardson P.C., Response to Restriction Requirement dated Jan. 13, 2011 in U.S. Appl. No. 12/161,733, filed Jul. 7, 2011, 1 page.
Klarquist Sparkman, LLP, Amendment and Reply to Office Action dated Dec. 20, 2010 in U.S. Appl. No. 12/296,193, filed Jun. 20, 2011, 24 pages.
Campo et al., "Comparative activity of Sant7 and anti-IL-6, IL-6R monoclonal antibodies in a murine model of B-cell lymphoma," *Cytokine*, 31(5):368-74 (2005).
Idezawa et al., "Interleukin-6 Functions as an Autocrine Invasion Factor of Human Pancreatic Cancer Cells," *Yamanashi Med. J.*, 19(2):53-67 (2004).
Idezawa et al., "Interleukin-6 Functions as an Autocrine Invasion Factor of Human Pancreatic Cancer Cells," *Yamanashi Med. J.*, 20(2):xxxvi (2005).
Kamohara et al., "IL-6 no Suigan Saibo no Zoshoku-Ten'i Oyobosu Eikyo to Kanshitsu Saibo ni yoru Hatsugen Seigyo Kiko," *Japanese Journal of Gastroenterological Surgery*, 39(7):1356 (Abstract 2529) (2006).
Tisdale, MJ., "Biology of cachexia," *J. Natl. Cancer Inst.*, 89(23):1763-73 (1997).
USPTO Non-Final Office Action in U.S. Appl. No. 12/161,733, dated Aug. 16, 2011, 20 pages.
European Search Report for App. Ser. No. 07 741 181.7, mailed Dec. 23, 2009, 6 pages.
International Search Report for App. Ser. No. PCT/JP2009/060314, mailed Aug. 11, 2009, 7 pages.
International Preliminary Report on Patentability for App. Ser. No. PCT/JP2009/060314, mailed Jan. 11, 2011, 8 pages.
European Search Report for App. Ser. No. 08 703 686.9, mailed Aug. 24, 2010, 12 pages.
Patel et al., "Endogenous interleukin-6 enhances the renal injury, dysfunction, and inflammation caused by ischemia/reperfusion," J. Pharmacol. Exp. Ther., 312(3):1170-1178 (2005).
Skurkovich et al., "Anticytokine therapy—new approach to the treatment of autoimmune and cytokine-disturbance diseases," Med. Hypotheses, 59(6):770-780 (2002) (In the Russian language. Relevant portions are in the English language).

(56) References Cited

OTHER PUBLICATIONS

Fish & Richardson P.C., Amendment in Reply to Office Action dated May 3, 2011 in U.S. Appl. No. 12/090,061, filed Nov. 1, 2011, 11 pages.
USPTO Non-Final Office Action in U.S. Appl. No. 12/094,644, dated Sep. 26, 2011, 6 pages.
USPTO Non-Final Office Action in U.S. Appl. No. 12/524,041, dated Aug. 29, 2011, 6 pages.
Ono et al., "The effect of IL-6 on the des-gamma-carboxy prothrombin synthesis in human hepatoma cells," *Gastroenterologia Japonica*, 27(6):745-50 (1992).
Q&A de wakaru himan to tounyoubyou, 3(6):982-984 (2004) (with English translation).
USPTO Non-Final Office Action in U.S. Appl. No. 12/090,061, dated Jan. 12, 2012, 8 pages.
Fish & Richardson P.C., Amendment and Reply to Office Action dated Aug. 16, 2011 in U.S. Appl. No. 12/161,733, filed Feb. 15, 2012, 13 pages.
Klarquist Sparkman, LLP, Amendment and Reply to Office Action dated Jul. 26, 2011 in U.S. Appl. No. 12/296,193, filed on Jan. 26, 2012, 10 pages.
Hirota et al., "Loss of a gp130 cardiac muscle cell survival pathway is a critical event in the onset of heart failure during biomechanical stress," *Cell* 97(2):189-98 (1999).
Ashizawa et al., "Clinical significance of interleukin-6 (IL-6) in the spread of gastric cancer: role of IL-6 as a prognostic factor," *Gastric Cancer*, 8:124-131 (2005).
Beck et al., "Brief report: alleviation of systemic manifestations of Castleman's disease by monoclonal anti-interleukin-6 antibody," *N. Engl. J Med.*, 330:602-605 (1994).
Bond et al., "Synergistic upregulation of metalloproteinase-9 by growth factors and inflammatory cytokines: an absolute requirement for transcription factor NF-kappa B," *FEBS Lett.*, 435:29-34 (1998).
Campochiaro, "Retinal and choroidal neovascularization," *J Cell Physiol.*, 184:301-310 (2000).
Choy et al., "Inhibiting interleukin-6 in rheumatoid arthritis," *Curr. Rheumatol. Rep.*, 10(5):413-7 (2008).
Chuntharapai et al., "Generation of monoclonal antibodies to chemokine receptors," *Methods Enzymol.*, 288:15-27 (1997).
Ewert et al., "Stability improvement of antibodies for extracellular and intracellular applications: CDR grafting to stable frameworks and structure-based framework engineering," *Methods*, 34:184-199 (2004).
Fujita et al., "Anti-interleukin-6 receptor antibody prevents muscle atrophy in colon-26 adenocarcinoma-bearing mice with modulation of lysosomal and ATP-ubiquitin-dependent proteolytic pathways," *Int. J. Cancer*, 68(5):637-643 (1996).
Gao et al., "Mutations in the EGFR kinase domain mediate STAT3 activation via IL-6 production in human lung adenocarcinomas," *J. Clin. Invest.*, 117(12):3846-3856 (2007).
Ghosh et al., "Missing pieces in the NF-kappaB puzzle," *Cell*, 109:S81-S96 (2002).
Greenberg et al., "Interleukin 6 reduces lipoprotein lipase activity in adipose tissue of mice in vivo and in 3T3-L1 adipocytes: a possible role for interleukin 6 in cancer cachexia," *Cancer Res.*, 52(15):4113-4116 (1992).
Greten et al., "IKKbeta links inflammation and tumorigenesis in a mouse model of colitis-associated cancer," *Cell*, 118:285-296 (2004).
Guerne et al., "Synovium as a source of interleukin 6 in vitro. Contribution to local and systemic manifestations of arthritis," *J Clin. Invest.*, 83(2):585-92 (1989).
Guillen et al., "Cytokine signaling during myocardial infarction: sequential appearance of IL-1 beta and IL-6," *Am. J Physiol.*, 269(2 Pt 2):R229-35 (1995).
Hanes et al., "Picomolar affinity antibodies from a fully synthetic naive library selected and evolved by ribosome display," *Nat. Biotechnol.*, 18(12):1287-92 (2000).

Hirano et al., "Excessive production of interleukin 6/B cell stimulatory factor-2 in rheumatoid arthritis," *Eur. J Immunol.*, 18(11):1797-801 (1988).
Houssiau et al., "Interleukin-6 in synovial fluid and serum of patients with rheumatoid arthritis and other inflammatory arthritides," *Arthritis Rheum.*, 31(6):784-8 (1988).
Karin et al., "NF-kappaB at the crossroads of life and death," *Nat. Immunol.*, 3(3):221-227 (2002).
Karin et al., "NF-kappaB in cancer: from innocent bystander to major culprit," *Nat. Rev. Cancer*, 2:301-310 (2002).
Kishimoto, "The biology of interleukin-6," *Blood*, 74(1):1-10 (1989).
Kotake et al., "Interleukin-6 and soluble interleukin-6 receptors in the synovial fluids from rheumatoid arthritis patients are responsible for osteoclast-like cell formation," *J. Bone Miner Res.*, 11(1):88-95 (1996).
Madhok et al., "Serum interleukin 6 levels in rheumatoid arthritis: correlations with clinical and laboratory indices of disease activity," *Ann. Rheum. Dis.*, 52(3):232-4 (1993).
Maeda et al., "IKKbeta couples hepatocyte death to cytokine-driven compensatory proliferation that promotes chemical hepatocarcinogenesis," *Cell*, 121:977-990 (2005).
Maeda et al., "Ikappa B kinasebeta/nuclear factor-kappaB activation controls the development of liver metastasis by way of interleukin-6 expression," *Hepatology*, 50:1851-1860 (2009).
Matzaraki et al., "Evaluation of serum procalcitonin and interleukin-6 levels as markers of liver metastasis," *Clin. Biochem.*, 40:336-342 (2007).
Naugler et al., "Gender disparity in liver cancer due to sex differences in MyD88-dependent IL-6 production," *Science*, 317:121-124 (2007).
Nishimoto et al., "Anti-interleukin 6 receptor antibody treatment in rheumatic disease," *Ann Rheum. Dis.*, 59 Suppl 1:i21-27 (2000).
Nishimoto et al., "Interleukin 6: from bench to bedside," *Nat. Clin. Pract. Rheumatol.*, 2(11):619-26 (2006).
Ohtsuka et al., "Relation of circulating interleukin-6 to left ventricular remodeling in patients with reperfused anterior myocardial infarction," *Clin. Cardiol.*, 27(7):417-420 (2004).
Pikarsky et al., "Nf-kappaB functions as a tumour promoter in inflammation-associated cancer," *Nature*, 431:461-466 (2004).
Puhakka et al., "Interleukin-6 and tumor necrosis factor alpha in relation to myocardial infarct size and collagen formation," *J. Card. Fail.*, 9(4):325-332 (2003).
Sack et al., "Interleukin-6 in synovial fluid is closely associated with chronic synovitis in rheumatoid arthritis," *Rheumatol. Int.*, 13(2):45-51 (1993).
Sansone et al., "IL-6 triggers malignant features in mammospheres from human ductal breast carcinoma and normal mammary gland," *J Clin. Invest.*, 117(12):3988-4002 (2007).
Sarkar et al., "Back to the future: COX-2 inhibitors for chemoprevention and cancer therapy," *Mini Rev. Med. Chem.*, 7:599-608 (2007).
Sato et al., "Reshaping a human antibody to inhibit the interleukin 6-dependent tumor cell growth," *Cancer*, 53:851-856 (1993).
Steeg et al., "Tumor metastasis: mechanistic insights and clinical challenges," *Nat. Med.*, 12(8):895-904 (2006).
Steeg, "Metastasis: A therapeutic target for cancer," *Nat. Clin. Pract. Oncol.*, 5(4):206-219 (2008).
Strassmann et al., "Evidence for the involvement of interleukin 6 in experimental cancer cachexia," *J. Clin. Invest.*, 89(5):1681-1684 (1992).
Studebaker et al., "Fibroblasts isolated from common sites of breast cancer metastasis enhance cancer cell growth rates and invasiveness in an interleukin-6-dependent manner," *Cancer Res.*, 68(21):9087-9095 (2008).
Takeda et al., "Murine tumor cells metastasizing selectively in the liver: ability to produce hepatocyte-activating cytokines interleukin-1 and/or -6," *Jpn. J. Cancer Res.*, 82:1299-1308 (1991).
Yamakawa et al., "Astrocytes promote the proliferation of lung cancer cells in brain metastases via inflammatory cytokines, especially IL-6," *Neuroscience*, 48(2/3):216, P-22 (poster presentation) (2009).
Fish & Richardson P.C., Amendment and Reply to Action dated Sep. 26, 2011 in U.S. Appl. No. 12/094,644, filed Mar. 21, 2012, 9 pages.

(56) References Cited

OTHER PUBLICATIONS

Klarquist Sparkman, LLP, Supplemental Amendment and Response in U.S. Appl. No. 12/296,193, filed on Mar. 19, 2012, 6 pages.
USPTO Final Office Action in U.S. Appl. No. 12/161,733, dated Apr. 9, 2012, 20 pages.
USPTO Non-Final Office Action in U.S. Appl. No. 12/094,644, dated May 22, 2012, 10 pages.
Fish & Richardson P.C., Amendment in Reply to Office Action dated Jan. 12, 2012 in U.S. Appl. No. 12/090,061, filed Jun. 11, 2012, 12 pages.
Sterne, Kessler, Goldstein & Fox P.L.L.C, Amendment and Reply to Office Action dated Aug. 29, 2011 in U.S. Appl. No. 12/524,041, filed on Jun. 20, 2012, 7 pages.
USPTO Non-Final Office Action in U.S. Appl. No. 12/996,162, dated Jun. 1, 2012, 8 pages.
International Preliminary Report on Patentability for App. Ser. No. PCT/JP2010/062874, mailed Feb. 7, 2012, 9 pages.
Fish & Richardson P.C., Amendment in Reply to Action dated Jun. 8, 2012, in U.S. Appl. No. 12/090,676, filed Jun. 29, 2012, 13 pages.
USPTO Restriction Requirement in U.S. Appl. No. 12/524,041, dated Aug. 29, 2011, 6 pages.
Sterne, Kessler, Goldstein & Fox P.L.L.C., Response to Restriction Requirement dated Aug. 29, 2011 in U.S. Appl. No. 12/524,041, filed on Oct. 28, 2011, 2 pages.
USPTO Non-Final Office Action in U.S. Appl. No. 12/524,041, dated Dec. 21, 2011, 7 pages.
International Search Report for App. Ser. No. PCT/JP2010/062874, mailed Aug. 31, 2010, 2 pages.
USPTO Notice of Allowance in U.S. Appl. No. 12/090,061, dated Aug. 27, 2012, 9 pages.
Fish & Richardson P.C., Amendment and Reply to Office Action dated Apr. 9, 2012 in U.S. Appl. No. 12/161,733, filed Oct. 9, 2012, 13 pages.
U.S. Appl. No. 12/090,676, filed Feb. 25, 2009.
U.S. Appl. No. 12/094,644, filed Feb. 27, 2009.
U.S. Appl. No. 12/161,733, filed Mar. 9, 2009.
U.S. Appl. No. 12/296,193, filed Apr. 15, 2009.
U.S. Appl. No. 12/524,041, filed Sep. 18, 2009.
U.S. Appl. No. 12/996,162, filed Mar. 7, 2011.
U.S. Appl. No. 13/387,292, filed Apr. 3, 2012.
U.S. Appl. No. 13/700,355, filed Apr. 2, 2013.
Ceyhan et al., "Neural invasion in pancreatic cancer: a mutual tropism between neurons and cancer cells," *Biochem. Biophys. Res. Commun.*, 374:442-447 (2008).
Hirai et al., "Perineural invasion in pancreatic cancer," *Pancreas*, 24(1):15-25 (2002).
Huang et al., "Inhibitory effect of AG490 on invasion and metastasis of human pancreatic cancer cells in vitro," *Chin. J Oncol.*, 28:890-892, Wanfang Data Co., Ltd., Beijing, China (2006) (in Chinese, with English abstract).
Huang et al., "Inhibition of STAT3 activity with AG490 decreases the invasion of human pancreatic cancer cells in vitro," *Cancer Sci.*, 97:1417-1423, Japanese Cancer Association, Tokyo, Japan (2006).
Maeda et al., "Essential Roles of IKKbeta / NF-kB Activation for Development of Liver Metastasis in Mice," Gastroenterol, 130:P-1-P-350, Supplement 2, AASLD Abstracts, p. A-750, abstract No. 107, Elsevier Inc. (2006).
Maeda et al., "Role of IKKbeta / NF-kB Activation for Development of Liver Metastasis," Supplement: The 58th Annual Meeting of the American Association for the Study of Liver Diseases, *Hepatol.*, 46:Issue Supplement Sl, AASLD Abstracts, p. 518A, abstract No. 630, American Association for the Study of Liver Diseases (2007).

Martignoni et al., "Role of mononuclear cells and inflammatory cytokines in pancreatic cancer-related cachexia," *Clin. Cancer Res.*, 11(16):5802-5808 (2005).
Miyamoto et al., "Interleukin-6 inhibits radiation induced apoptosis in pancreatic cancer cells," *Anticancer Res.*, 21:2449-2456 (2001).
Nishimoto et al., "Clinical studies in patients with Castleman's disease, Crohn's disease, and rheumatoid arthritis in Japan," *Clin. Rev. Allergy Immunol.*, 28(3):221-30 (2005).
Ogata et al., "Anti-IL-6 receptor antibody does not ameliorate radiation pneumonia in mice," *Exp. Ther. Med.*, 4:273-276 (2012).
Ogata et al., "Early administration of IL-6RA does not prevent radiation-induced lung injury in mice," *Radiat. Oncol.*, 5:26 (2010).
Ohsugi et al., "Pharmacological and Clinical Profile of Humanized Anti-human IL-6 Receptor Antibody (Tocilizumab), a Therapeutic Drug for Castleman's Disease," *Nihon Yakurigaku Zasshi*, 126(6):419-25 (Dec. 2005).
Okada et al., "Experimental implication of celiac ganglionotropic invasion of pancreatic-cancer cells bearing c-ret proto-oncogene with reference to glial-cell-line-derived neurotrophic factor (GDNF)," Int. J Cancer, 81:67-73 (1999).
Okada et al., "Elevated serum interleukin-6 levels in patients with pancreatic cancer," Japan J Clin. Oncol., 28:12-15, Foundation of Clinical Oncology, Tokyo, Japan (1998).
Rinsho Kensa, "Cytokines and immune network," 35(5):447-452 (1991) (with English translation).
Roitt et al., *Immunology, M. Mir*, p. 110 (2000) (with English translation).
Rudikoff et al., "Single amino acid substitution altering antigen-binding specificity," *Proc. Natl. Acad. Sci. U.S.A.*, 79(6):1979-83 (1982).
Takahashi et al., "Antiproteases in preventing the invasive potential of pancreatic cancer cells," *JOP*, 8(4 Suppl.):501-508 (2007).
Yokota et al., "Clinical study of tocilizumab in children with systemic-onset juvenile idiopathic arthritis," *Clin. Rev. Allergy Immunol.*, 28(3):231-8 (2005).
USPTO Final Office Action in U.S. Appl. No. 12/524,041, dated Oct. 15, 2012, 6 pages.
Sterne, Kessler, Goldstein & Fox P.L.L.C, Amendment and Reply to Office Action dated Oct. 15, 2012 in U.S. Appl. No. 12/524,041, filed on Jan. 15, 2013, 7 pages.
Sterne, Kessler, Goldstein & Fox P.L.L.C, Response to Restriction Requirement dated Jun. 1, 2012 in U.S. Appl. No. 12/996,162, filed on Jun. 28, 2012, 4 pages.
USPTO Non-Final Office Action in U.S. Appl. No. 12/996,162, dated Sep. 12, 2012, 8 pages.
USPTO Notice of Allowance in U.S. Appl. No. 12/090,061, dated Mar. 22, 2013, 9 pages.
USPTO Office Action in U.S. Appl. No. 12/524,041, dated Mar. 15, 2013, 5 pages.
Sterne, Kessler, Goldstein & Fox P.L.L.C, Amendment and Reply to Office Action dated Sep. 12, 2012 in U.S. Appl. No. 12/996,162, filed on Mar. 12, 2013, 14 pages.
USPTO Final Office Action in U.S. Appl. No. 12/996,162, dated Mar. 20, 2013, 11 pages.
USPTO Restriction Requirement in U.S. Appl. No. 13/387,292, dated Jan. 31, 2013, 8 pages.
Sterne, Kessler, Goldstein & Fox P.L.L.C, Response to Restriction Requirement dated Jan. 31, 2013 in U.S. Appl. No. 13/387,292, filed on Mar. 1, 2013, 2 pages.
USPTO Office Action in U.S. Appl. No. 13/387,292, dated Mar. 26, 2013, 7 pages.
International Preliminary Report on Patentability with Written Opinion for App. Ser. No. PCT/JP2008/050842, dated Jul. 28, 2009, 6 pages.
U.S. Appl. No. 13/700,355, filed Nov. 27, 2012, Nishimura.

\* cited by examiner

METHODS FOR SUPPRESSING ACUTE REJECTION OF A HEART TRANSPLANT

CROSS-REFERENCE TO RELATED APPLICATIONS

This application is the National Stage of International Application Serial No. PCT/JP2006/322726, filed on Nov. 15, 2006, which claims the benefit of Japanese Application Serial Nos. 2005-330637, filed on Nov. 15, 2005, and 2006-170950, filed on Jun. 21, 2006. The contents of the foregoing applications are hereby incorporated by reference in their entirety.

TECHNICAL FIELD

The present invention relates to agents for suppressing the induction of cytotoxic T cells (killer T cells), which comprise IL-6 inhibitors as active ingredients, and uses thereof. The present invention also relates to methods for suppressing rejections after transplantation, which comprise the step of administering IL-6 inhibitors to recipients.

BACKGROUND ART

IL-6 is a cytokine called B-cell stimulating factor 2 (BSF2) or interferon β2. IL-6 was discovered as a differentiation factor involved in the activation of B-cell lymphocytes (Non-Patent Document 1), and was later revealed to be a multifunctional cytokine that influences the function of various cells (Non-Patent Document 2). IL-6 has been reported to induce maturation of T lymphocyte cells (Non-Patent Document 3).

IL-6 transmits its biological activity via two kinds of proteins on the cell. The first kind of protein is the IL-6 receptor, which is a ligand binding protein to which IL-6 binds; it has a molecular weight of about 80 kDa (Non-Patent Documents 4 and 5). The IL-6 receptor is present in a membrane-bound form that penetrates and is expressed on the cell membrane, and also as a soluble IL-6 receptor, which mainly consists of the extracellular region of the membrane-bound form.

The other kind of protein is the membrane protein gp130, which has a molecular weight of about 130 kDa and is involved in non-ligand binding signal transduction. The biological activity of IL-6 is transmitted into the cell through formation of an IL-6/IL-6 receptor complex by IL-6 and 11-6 receptor followed by binding of the complex with gp130 (Non-Patent Document 6).

IL-6 inhibitors are substances that inhibit the transmission of IL-6 biological activity. Currently, known IL-6 inhibitors include antibodies against IL-6 (anti-IL-6 antibodies), antibodies against IL-6 receptor (anti-IL-6 receptor antibodies), antibodies against gp 130 (anti-gp130 antibodies), IL-6 variants, partial peptides of IL-6 or IL-6 receptor, and such.

There are several reports regarding anti-IL-6 receptor antibodies (Non-Patent Documents 7 and 8; and Patent Documents 1-3). One such report details a humanized PM-1 antibody, which is obtained by transplanting the complementarity determining region (CDR) of mouse antibody PM-1 (Non-Patent Document 9), which is an anti-IL-6 receptor antibody, into a human antibody (Patent Document 4).

IL-6 is known to serve as a killer cell helper factor (KHF) involved in the induction of cytotoxic T cells (Non-Patent Document 10). In-vitro experiments using human rIL-6 show that in the presence of IL-2, rIL-6 induces the differentiation of cytotoxic T cells from human peripheral blood T cells and CD4-/CD8- or CD4-/CD8+ thymus T cells. IL-6 is also known to function in vivo as a cytotoxic T cell differentiation-inducing factor (Non-Patent Document 11).

However, various other cytokines in addition to IL-6 are also known to function as KHFs in vivo, and to date there have been no reports clarifying whether or not IL-6 inhibitors can suppress the induction of cytotoxic T cells in vivo.

The prior-art documents related to the present invention are shown below.

Non-Patent Document 1: Hirano, T. et al., Nature (1986) 324, 73-76
Non-Patent Document 2: Akira, S. et al., Adv. in Immunology (1993) 54, 1-78
Non-Patent Document 3: Lotz, M. et al., J. Exp. Med. (1988) 167, 1253-1258
Non-Patent Document 4: Taga, T. et al., J. Exp. Med. (1987) 166, 967-981
Non-Patent Document 5: Yamasaki, K. et al., Science (1988) 241, 825-828
Non-Patent Document 6: Taga, T. et al., Cell (1989) 58, 573-581
Non-Patent Document 7: Novick, D. et al., Hybridoma (1991) 10, 137-146
Non-Patent Document 8: Huang, Y. W. et al., Hybridoma (1993) 12, 621-630
Non-Patent Document 9: Hirata, Y. et al., J. Immunol. (1989) 143, 2900-2906
Non-Patent Document 10: Okada M. et al., J. Immunology 141:1543-1549, 1988
Non-Patent Document 11: Kitahara M. et al, Jpn. J. Cancer Res. 81:1032-1038.1990
Patent Document 1: WO 95/09873
Patent Document 2: French Patent Application No. FR 2694767
Patent Document 3: U.S. Pat. No. 5,216,128
Patent Document 4: WO 92/19759

DISCLOSURE OF THE INVENTION

Problems to be Solved by the Invention

The present invention has been conducted under the circumstances described above. An objective of the present invention is to provide agents for suppressing the induction of cytotoxic T cells, which comprise IL-6 inhibitors as active ingredients.

A further objective of the present invention is to provide methods for suppressing rejections after transplantation, which comprise the step of administering IL-6 inhibitors to subjects.

Means for Solving the Problems

To achieve the objectives described above, the present inventors tested anti-IL-6 receptor antibodies for the effect of suppressing cytotoxic T cell induction.

First, the present inventors intraperitoneally administered cells of the mastocytoma line P815 into C57BL/6 mice. The inventors also intraperitoneally administered cells of the EL4 lymphoma cell line to BALB/c mice as immunizing cells (alloantigens). Spleens were isolated from these mice, and the splenic cells (effector cells) were cultured at various effector cell/target cell (E/T) ratios, where the above-described immunizing cells were used as target cells, and the CTL activity (cytotoxic T cell activity) per target cell was measured. Then, an anti-IL-6 receptor antibody or rat IgG (control antibody)

was administered to a mouse model having the above-described alloantigens, and CTL activity was assayed under the same conditions.

The result of the above assays showed that CTL activity towards the alloantigens was statistically significantly reduced in mice treated with the anti-IL-6 receptor antibody, as compared with untreated mice and mice treated with the control antibody (FIGS. 1 to 4). These results clarified that anti-IL-6 receptor antibodies have the function of suppressing cytotoxic T cell induction.

The present inventors also assessed the effect of administering anti-IL-6 receptor antibodies to an allogenic mouse heart transplantation model. As a result, administering anti-IL-6 receptor antibodies suppressed acute heart transplant rejection and statistically significantly prolonged the survival of transplanted hearts. Further, the inventors histopathologically examined transplanted hearts isolated from recipients five days after transplantation. The results showed that in the group treated with anti-IL-6 receptor antibodies, the infiltration of inflammatory cells into transplanted heart tissues was significantly suppressed, and cardiomyocytes were relatively preserved.

Thus, the present inventors discovered for the first time that administering anti-IL-6 receptor antibodies can suppress cytotoxic T cell induction and suppress rejections after transplantation, and they thus completed the present invention.

More specifically, the present invention provides the following inventions:

[1] an agent for suppressing the induction of a cytotoxic T cell, which comprises an IL-6 inhibitor as an active ingredient.

[2] the agent of [1], wherein the IL-6 inhibitor is an antibody that recognizes an IL-6.

[3] the agent of [1], wherein the IL-6 inhibitor is an antibody that recognizes an IL-6 receptor.

[4] the agent of [2] or [3], wherein the antibody is a monoclonal antibody.

[5] the agent of [2] or [3], wherein the antibody recognizes a human IL-6 or a human IL-6 receptor.

[6] the agent of [2] or [3], wherein the antibody is a recombinant antibody.

[7] the agent of [6], wherein the antibody is a chimeric antibody, humanized antibody, or human antibody.

[8] the agent of [1], which is used to suppress rejection after transplantation.

[9] an agent for suppressing rejection in heart transplantation, which comprises an IL-6 inhibitor as an active ingredient.

[10] the agent of [9], wherein the IL-6 inhibitor is an antibody that recognizes an IL-6.

[11] the agent of [9], wherein the IL-6 inhibitor is an antibody that recognizes an IL-6 receptor.

[12] the agent of [10] or [11], wherein the antibody is a monoclonal antibody.

[13] the agent of [10] or [11], wherein the antibody recognizes a human IL-6 or a human IL-6 receptor.

[14] the agent of [10] or [11], wherein the antibody is a recombinant antibody.

[15] the agent of [14], wherein the antibody is a chimeric antibody, humanized antibody, or human antibody.

[16] the agent of [9], which is used to suppress acute rejection in heart transplantation;

[17] a method for suppressing the induction of a cytotoxic T cell, which comprises the step of administering an IL-6 inhibitor to a subject;

[18] the method of [17], wherein the IL-6 inhibitor is an antibody that recognizes an IL-6;

[19] the method of [17], wherein the IL-6 inhibitor is an antibody that recognizes an IL-6 receptor;

[20] the method of [18] or [19], wherein the antibody is a monoclonal antibody;

[21] the method of [18] or [19], wherein the antibody is an antibody that recognizes a human IL-6 or a human IL-6 receptor;

[22] the method of [18] or [19], wherein the antibody is a recombinant antibody;

[23] the method of [22], wherein the antibody is a chimeric antibody, humanized antibody, or human antibody;

[24] the method of [17], which is used to suppress rejection after transplantation;

[25] use of an IL-6 inhibitor in the production of an agent for suppressing the induction of a cytotoxic T cell;

[26] the use of [25], wherein the IL-6 inhibitor is an antibody that recognizes an IL-6;

[27] the use of [25], wherein the IL-6 inhibitor is an antibody that recognizes an IL-6 receptor;

[28] the use of [26] or [27], wherein the antibody is a monoclonal antibody;

[29] the use of [26] or [27], wherein the antibody recognizes a human IL-6 or a human IL-6 receptor;

[30] the use of [26] or [27], wherein the antibody is a recombinant antibody;

[31] the use of [30], wherein the antibody is a chimeric antibody, humanized antibody, or human antibody;

[32] a method for suppressing rejection in heart transplantation, which comprises the step of administering an IL-6 inhibitor to a subject;

[33] the method of [32], wherein the IL-6 inhibitor is an antibody that recognizes an IL-6;

[34] the method of [32], wherein the IL-6 inhibitor is an antibody that recognizes an IL-6 receptor;

[35] the method of [33] or [34], wherein the antibody is a monoclonal antibody;

[36] the method of [33] or [34], wherein the antibody recognizes a human IL-6 or a human IL-6 receptor;

[37] the method of [33] or [34], wherein the antibody is a recombinant antibody;

[38] the method of [37], wherein the antibody is a chimeric antibody, humanized antibody, or human antibody;

[39] the method of [32], which is used to suppress acute rejection in heart transplantation;

[40] use of an IL-6 inhibitor in the production of an agent for suppressing rejection in heart transplantation;

[41] the use of [40], wherein the IL-6 inhibitor is an antibody that recognizes an IL-6;

[42] the use of [40], wherein the IL-6 inhibitor is an antibody that recognizes an IL-6 receptor;

[43] the use of [41] or [42], wherein the antibody is a monoclonal antibody;

[44] the use of [41] or [42], wherein the antibody recognizes a human IL-6 or a human IL-6 receptor;

[45] the use of [41] or [42], wherein the antibody is a recombinant antibody; and

[46] the use of [45], wherein the antibody is a chimeric antibody, humanized antibody, or human antibody.

BEST MODE FOR CARRYING OUT THE INVENTION

Figure 1:
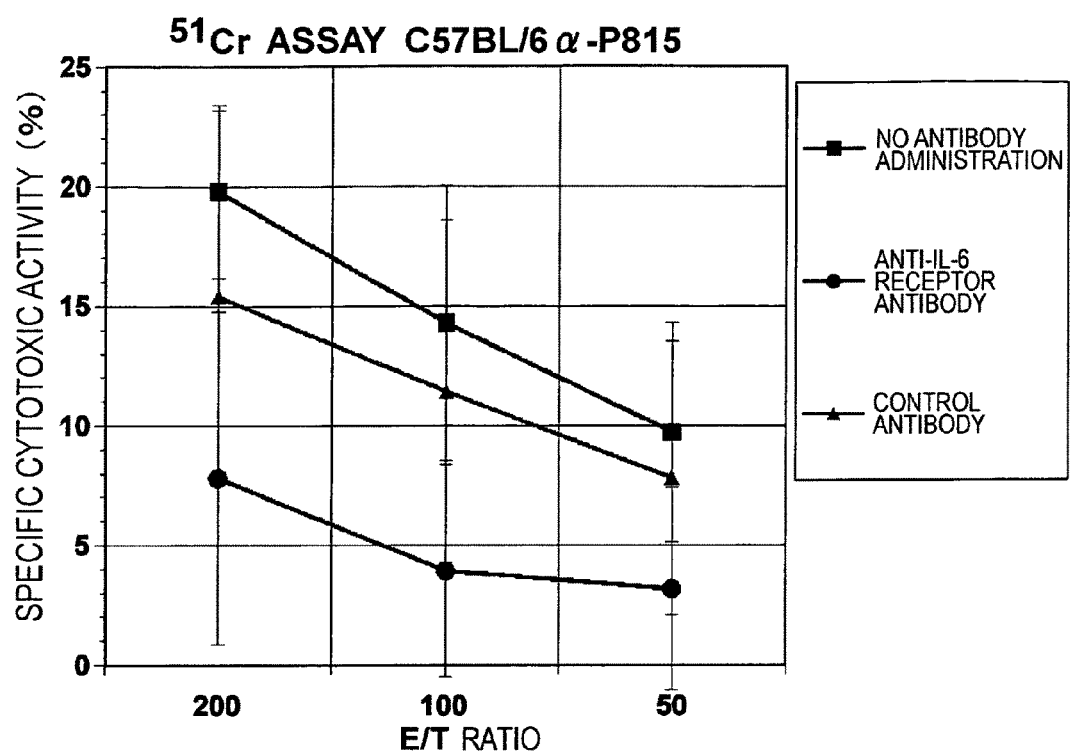
FIG. 1 shows the specific cytotoxic activity (cytotoxic T lymphocyte activity; CTL activity) for each E/T ratio in mice not treated with an antibody, mice treated with an anti-IL-6 receptor antibody, and mice treated with a control antibody, where each was administered with cells of the mastocytoma line P815.

The present inventors discovered that administration of an anti-IL-6 receptor antibody can suppress cytotoxic T cell induction. The present invention is based on these findings.

The present invention relates to agents for suppressing cytotoxic T cell induction, which comprise an IL-6 inhibitor as an active ingredient.

Herein, an "IL-6 inhibitor" is a substance that blocks IL-6-mediated signal transduction and inhibits IL-6 biological activity. Preferably, the IL-6 inhibitor is a substance that has inhibitory function against the binding of IL-6, IL-6 receptor, or gp130.

The IL-6 inhibitors of the present invention include, but are not limited to, for example, anti-IL-6 antibodies, anti-IL-6 receptor antibodies, anti-gp130 antibodies, IL-6 variants, soluble IL-6 receptor variants, and partial peptides of IL-6 or IL-6 receptor and low molecular weight compounds that show similar activities. Preferable IL-6 inhibitors of the present invention include antibodies that recognize IL-6 receptors.

The source of the antibodies is not particularly restricted in the present invention; however, the antibodies are preferably derived from mammals, and more preferably derived from humans.

The anti-IL-6 antibodies used in the present invention can be obtained as polyclonal or monoclonal antibodies using known means. In particular, monoclonal antibodies derived from mammals are preferred as the anti-IL-6 antibodies used in the present invention. Monoclonal antibodies derived from mammals include those produced from hybridomas and those produced by genetic engineering methods from hosts transformed with an expression vector that comprises an antibody gene. By binding to IL-6, the antibody inhibits IL-6 from binding to an IL-6 receptor and thus blocks the transmission of IL-6 biological activity into the cell.

Such antibodies include, MH166 (Matsuda, T. et al., Eur. J. Immunol. (1988) 18, 951-956), SK2 antibody (Sato, K. et al., transaction of the 21$^{st}$ Annual Meeting of the Japanese Society for Immunology (1991) 21, 166), and so on.

Basically, hybridomas that produce anti-IL-6 antibodies can be prepared using known techniques, as follows: Specifically, such hybridomas can be prepared by using IL-6 as a sensitizing antigen to carry out immunization using a conventional immunization method, fusing the obtained immune cells with known parent cells by a conventional cell fusion method, and screening for monoclonal antibody-producing cells using a conventional screening method.

More specifically, anti-IL-6 antibodies can be produced as follows: For example, human IL-6 for use as the sensitizing antigen for obtaining antibodies can be obtained using the IL-6 gene and/or amino acid sequences disclosed in Eur. J. Biochem. (1987) 168, 543-550; J. Immunol. (1988) 140, 1534-1541; and/or Agr. Biol. Chem. (1990) 54, 2685-2688.

After transforming an appropriate host cell with a known expression vector system inserted with an IL-6 gene sequence, the desired IL-6 protein is purified using known methods from the inside of the host cell or from the culture supernatant. This purified IL-6 protein may be used as a sensitizing antigen. Alternatively, a fusion protein of the IL-6 protein and another protein may be used as a sensitizing antigen.

Anti-IL6 receptor antibodies used for the present invention can be obtained as polyclonal or monoclonal antibodies by using known methods. In particular, the anti-IL-6 receptor antibodies used in the present invention are preferably monoclonal antibodies derived from mammals. The monoclonal antibodies derived from mammals include those produced from hybridomas and those produced using genetic engineering methods from hosts transformed with an expression vector that comprises an antibody gene. By binding to an IL-6 receptor, the antibody inhibits IL-6 from binding to the IL-6 receptor, and thus blocks the transmission of IL-6 biological activity into the cell.

Such antibodies include, MR16-1 antibody (Tamura, T. et al., Proc. Natl. Acad. Sci. USA (1993) 90, 11924-11928); PM-1 antibody (Hirata, Y. et al., J. Immunol. (1989) 143, 2900-2906); AUK12-20 antibody, AUK64-7 antibody and AUK146-15 antibody (WO 92/19759); and so on. Of these, the PM-1 antibody can be exemplified as a preferred monoclonal antibody against the human IL-6 receptor, and the MR16-1 antibody as a preferred monoclonal antibody against the mouse IL-6 receptor.

Basically, hybridomas producing an anti-IL-6 receptor monoclonal antibody can be prepared using known techniques, as follows: Specifically, such hybridomas can be prepared by using an IL-6 receptor as the sensitizing antigen to carry out immunization by a conventional immunization method, fusing the obtained immune cells with a known parent cell using a conventional cell fusion method, and screening for monoclonal antibody-producing cells using a conventional screening method.

More specifically, anti-IL-6 receptor antibodies can be produced as follows: For example, a human IL-6 receptor or mouse IL-6 receptor for use as a sensitizing antigen for obtaining antibodies can be obtained by using the IL-6 receptor genes and/or amino acid sequences disclosed in European Patent Application Publication No. EP 325474 and Japanese Patent Application Kokai Publication No. (JP-A) Hei 3-155795, respectively.

There are two kinds of IL-6 receptor proteins: one expressed on the cell membrane and the other separated from the cell membrane (soluble IL-6 receptors) (Yasukawa, K. et al., J. Biochem. (1990) 108, 673-676). The soluble IL-6 receptor essentially consists of the extracellular region of the cell membrane-bound IL-6 receptor, and differ from the membrane-bound IL-6 receptor in that it lacks the transmembrane region or both the transmembrane and intracellular regions. Any IL-6 receptor may be employed as an IL-6 receptor protein, so long as it can be used as a sensitizing antigen for producing an anti-IL-6 receptor antibody used in the present invention.

After transforming an appropriate host cell with a known expression vector system inserted with an IL-6 receptor gene sequence, the desired IL-6 receptor protein is purified from the inside of the host cell or from the culture supernatant using a known method. This purified IL-6 receptor protein may be used as a sensitizing antigen. Alternatively, a cell expressing the IL-6 receptor or a fusion protein of the IL-6 receptor protein and another protein may be used as a sensitizing antigen.

Anti-gp130 antibodies used in the present invention can be obtained as polyclonal or monoclonal antibodies by using known methods. In particular, the anti-gp130 antibodies used in the present invention are preferably monoclonal antibodies derived from mammals. Mammal-derived monoclonal antibodies include those produced from hybridomas and those produced using genetic engineering methods from hosts transformed with an expression vector that comprises an antibody gene. By binding to gp130, the antibody inhibits gp130 from binding to the IL-6/IL-6 receptor complex, and thus blocks transmission of IL-6 biological activity into the cell.

Such antibodies include, AM64 antibody (JP-A Hei 3-219894); 4B11 antibody and 2H4 antibody (U.S. Pat. No. 5,571,513); B-S12 antibody and B-P8 antibody (JP-A Hei 8-291199); and so on.

Basically, anti-gp130 monoclonal antibody-producing hybridomas can be prepared using known techniques, as follows: Specifically, such hybridomas can be prepared by using gp130 as a sensitizing antigen to carry out the immunization using a conventional immunization method, fusing the obtained immune cells with a known parent cell by a conventional cell fusion method, and screening for monoclonal antibody-producing cells using a conventional screening method.

More specifically, monoclonal antibodies can be produced as follows: For example, gp130 for use as a sensitizing antigen for obtaining antibodies can be obtained using the gp130 gene and/or amino acid sequence disclosed in European Patent Application Publication No. EP 411946.

After transforming an appropriate host cell with a known expression vector system inserted with a gp130 gene sequence, the desired gp130 protein is purified by a known method from the inside of the host cell or from the culture supernatant. This purified gp130 protein may be used as a sensitizing antigen. Alternatively, a cell expressing gp130 or a fusion protein of the gp130 protein and another protein may be used as a sensitizing antigen.

Mammals to be immunized with a sensitizing antigen are not particularly limited, but are preferably selected in consideration of compatibility with the parent cell used for cell fusion. Generally, rodents such as mice, rats, and hamsters are used.

Animals are immunized with sensitizing antigens according to known methods. For example, as a general method, animals are immunized by intraperitoneal or subcutaneous injection of a sensitizing antigen. Specifically, the sensitizing antigen is preferably diluted or suspended in an appropriate amount of phosphate-buffered saline (PBS), physiological saline or such, mixed with an appropriate amount of a general adjuvant (e.g., Freund's complete adjuvant), emulsified, and then administered to a mammal several times, every four to 21 days. In addition, an appropriate carrier may be used for immunization with a sensitizing antigen.

Following such immunization, an increased level of a desired antibody in serum is confirmed and then immune cells are obtained from the mammal for cell fusion. Preferred immune cells for cell fusion include, in particular, spleen cells.

The mammalian myeloma cells used as parent cells, i.e. as partner cells to be fused with the above immune cells, include various known cell strains, for example, P3X63Ag8.653 (Kearney, J. F. et al., J. Immunol (1979) 123, 1548-1550), P3X63Ag8U.1 (Current Topics in Microbiology and Immunology (1978) 81, 1-7), NS-1 (Kohler, G and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), F0 (de St. Groth, S. F. et al., J. Immunol. Methods (1980) 35, 1-21), S194 (Trowbridge, I. S., J. Exp. Med. (1978) 148, 313-323), R210 (Galfre, G et al., Nature (1979) 277, 131-133), and such.

Basically, cell fusion of the aforementioned immune cells and myeloma cells can be performed using known methods, for example, the method of Milstein et al. (Kohler, G. and Milstein, C., Methods Enzymol. (1981) 73, 3-46), and such.

More specifically, the aforementioned cell fusion is achieved in general nutrient culture medium in the presence of a cell fusion enhancing agent. For example, polyethylene glycol (PEG), Sendai virus (HVJ), and such are used as fusion enhancing agents. Further, to enhance fusion efficiency, auxiliary agents such as dimethyl sulfoxide may be added depending on needs.

The ratio of immune cells to myeloma cells used is preferably, for example, 1 to 10 immune cells for each myeloma cell. The culture medium used for the aforementioned cell fusion is, for example, the RPMI 1640 or MEM culture medium, which are suitable for proliferation of the aforementioned myeloma cells. A general culture medium used for culturing this type of cell can also be used. Furthermore, serum supplements such as fetal calf serum (FCS) can be used in combination.

For cell fusion, the fusion cells (hybridomas) of interest are formed by mixing predetermined amounts of an aforementioned immune cell and myeloma cell in an aforementioned culture medium, and then adding and mixing a concentration of 30% to 60% (w/v) PEG solution (e.g., a PEG solution with a mean molecular weight of about 1,000 to 6,000) pre-heated to about 37° C. Then, cell fusion agents and such that are unsuitable for the growth of hybridomas can be removed by repeatedly adding an appropriate culture medium and then removing the supernatant by centrifugation.

The above hybridomas are selected by culturing cells in a general selection culture medium, for example, HAT culture medium (a culture medium containing hypoxanthine, aminopterin, and thymidine). Culture in HAT culture medium is continued for a sufficient period, generally several days to several weeks, to kill cells other than the hybridomas of interest (unfused cells). Then, a standard limited dilution method is performed to screen and clone hybridomas that produce an antibody of interest.

In addition to the methods for immunizing non-human animals with antigens for obtaining the aforementioned hybridomas, desired human antibodies with the activity of binding to a desired antigen or antigen-expressing cell can be obtained by sensitizing a human lymphocyte with a desired antigen protein or antigen-expressing cell in vitro, and fusing the sensitized B lymphocyte with a human myeloma cell (e.g., U266) (see, Japanese Patent Application Kokoku Publication No. (JP-B) Hei 1-59878 (examined, approved Japanese patent application published for opposition)). Further, a desired human antibody can be obtained by administering an antigen or antigen-expressing cell to a transgenic animal that has a repertoire of human antibody genes, and then following the aforementioned method (see, International Patent Application Publication Nos. WO 93/12227, WO 92/03918, WO 94/02602, WO 94/25585, WO 96/34096, and WO 96/33735).

The thus-prepared hybridomas which produce monoclonal antibodies can be subcultured in a conventional culture medium and stored in liquid nitrogen for a long period.

When obtaining monoclonal antibodies from the aforementioned hybridomas, the following methods may be employed: (1) methods where the hybridomas are cultured according to conventional methods and the antibodies are obtained as a culture supernatant; (2) methods where the hybridomas are proliferated by administering them to a compatible mammal and the antibodies are obtained as ascites; and so on. The former method is preferred for obtaining antibodies with high purity, and the latter is preferred for large-scale antibody production.

For example, anti-IL-6 receptor antibody-producing hybridomas can be prepared by the method disclosed in JP-A Hei 3-139293. Such hybridomas can be prepared by injecting a PM-1 antibody-producing hybridoma into the abdominal cavity of a BALB/c mouse, obtaining ascites, and then purifying a PM-1 antibody from the ascites; or by culturing the hybridoma in an appropriate medium (e.g., RPMI1640 medium containing 10% fetal bovine serum, and 5% BM-Condimed H1 (Boehringer Mannheim); hybridoma SFM medium (GIBCO-BRL); PFHM-II medium (GIBCO-BRL), etc.) and then obtaining PM-1 antibody from the culture supernatant.

Recombinant antibodies can be used as the monoclonal antibodies of the present invention, wherein the antibodies are produced using genetic recombination techniques by cloning an antibody gene from a hybridoma, inserting the gene into an appropriate vector, and then introducing the vector into a host (see, for example, Borrebaeck, C. A. K. and Larrick, J. W., Therapeutic Monoclonal Antibodies, published in the United Kingdom by Macmillan Publishers Ltd, 1990).

More specifically, mRNAs coding for antibody variable (V) regions are isolated from cells that produce antibodies of interest, such as hybridomas. mRNAs can be isolated by preparing total RNAs according to known methods, such as the guanidine ultracentrifugation method (Chirgwin, J. M. et al., Biochemistry (1979) 18, 5294-5299) and the AGPC method (Chomczynski, P. et al., Anal. Biochem. (1987) 162, 156-159), and preparing mRNAs using the an MRNA Purification Kit (Pharmacia) and such. Alternatively, mRNAs can be directly prepared using a QuickPrep MRNA Purification Kit (Pharmacia).

cDNAs of the antibody V regions are synthesized from the obtained mRNAs using reverse transcriptase. cDNAs may be synthesized using an AMV Reverse Transcriptase First-strand cDNA Synthesis Kit and so on. Further, to synthesize and amplify the cDNAs, the 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) using 5'-Ampli FINDER RACE Kit (Clontech) and PCR may be employed. A DNA fragment of interest is purified from the obtained PCR products and then ligated with a vector DNA. Then, a recombinant vector is prepared using the above DNA and introduced into *Escherichia coli* or such, and then its colonies are selected to prepare a desired recombinant vector. The nucleotide sequence of the DNA of interest is confirmed by, for example, the dideoxy method.

When a DNA encoding the V region of an antibody of interest is obtained, the DNA is ligated with a DNA that encodes a desired antibody constant region (C region), and inserted into an expression vector. Alternatively, a DNA encoding an antibody V region may be inserted into an expression vector comprising a DNA of an antibody C region.

To produce an antibody to be used in the present invention, as described below, an antibody gene is inserted into an expression vector such that it is expressed under the control of an expression regulating region, for example, an enhancer and promoter. Then, the antibody can be expressed by transforming a host cell with this expression vector.

In the present invention, to reduce heteroantigenicity against humans and such, artificially modified genetic recombinant antibodies, for example, chimeric antibodies, humanized antibodies, or human antibodies, can be used. These modified antibodies can be prepared using known methods.

A chimeric antibody can be obtained by ligating a DNA encoding an antibody V region, obtained as above, with a DNA encoding a human antibody C region, then inserting the DNA into an expression vector and introducing it into a host for production (see, European Patent Application Publication No. EP 125023; International Patent Application Publication No. WO 92/19759). This known method can be used to obtain chimeric antibodies useful for the present invention.

Humanized antibodies are also referred to as reshaped human antibodies, and are antibodies wherein the complementarity determining regions (CDRs) of an antibody from a mammal other than human (e.g., a mouse antibody) are transferred into the CDRs of human antibodies. General methods for this gene recombination are also known (see, European Patent Application Publication No. EP 125023, International Patent Application Publication No. WO 92/19759).

More specifically, DNA sequences designed such that the CDRs of a mouse antibody are ligated with the framework regions (FRs) of a human antibody are synthesized by PCR from several oligonucleotides produced to contain overlapping portions at their termini. The obtained DNA is ligated with a human antibody C region-encoding DNA and then inserted into an expression vector. The expression vector is introduced into a host to produce the humanized antibody (see, European Patent Application Publication No. EP 239400, International Patent Application Publication No. WO 92/19759).

The human antibody FRs to be ligated via the CDRs are selected so that the CDRs form suitable antigen binding sites. The amino acid(s) within the FRs of the antibody variable regions may be substituted as necessary so that the CDRs of the reshaped human antibody form an appropriate antigen binding site (Sato, K. et al., Cancer Res. (1993) 53, 851-856).

Human antibody C regions are used for the chimeric and humanized antibodies, and include Cγ. For example, Cγ1, Cγ2, Cγ3, or Cγ4 may be used. Furthermore, to improve the stability of the antibodies or their production, the human antibody C regions may be modified.

Chimeric antibodies consist of the variable region of an antibody derived from a non-human mammal and the constant region of an antibody derived from a human; humanized antibodies consist of the CDRs of an antibody derived from a non-human mammal and the framework regions and constant regions derived from a human antibody. Both have reduced antigenicity in the human body, and are thus useful as antibodies for use in the present invention.

Preferred specific examples of humanized antibodies for use in the present invention include the humanized PM-1 antibody (see, International Patent Application Publication No. WO 92/19759).

Furthermore, in addition to the aforementioned methods for obtaining human antibodies, techniques for obtaining human antibodies by panning using a human antibody library are also known. For example, the variable regions of human antibodies can be expressed on phage surfaces as single chain antibodies (scFv) by using the phage display method, and antigen-binding phages can then be selected. By analyzing the genes of the selected phages, DNA sequences coding for the human antibody variable regions that bind to the antigen can be determined. Once the DNA sequence of an scFv that binds to the antigen is revealed, an appropriate expression vector comprising the sequence can be constructed to obtain an human antibody. These methods are already known, and the publications of WO 92/01047, WO 92/20791, WO93/06213, WO 93/11236, WO 93/19172, WO 95/01438, and WO 95/15388 can be used as reference.

The antibody genes constructed above can be expressed according to conventional methods. When a mammalian cell is used, the antibody gene can be expressed using a DNA in which the antibody gene to be expressed is functionally ligated to a useful commonly used promoter and a poly A signal downstream of the antibody gene, or a vector comprising the DNA. Examples of a promoter/enhancer include the human cytomegalovirus immediate early promoter/enhancer.

Furthermore, other promoters/enhancers that can be used for expressing the antibodies for use in the present invention include viral promoters/enhancers from retroviruses, polyoma viruses, adenoviruses, simian virus 40 (SV40), and such; and also include mammalian cell-derived promoters/enhancers such as human elongation factor 1α (HEF 1α).

For example, when the SV40 promoter/enhancer is used, the expression can be easily performed by following the method by Mulligan et al. (Mulligan, R. C. et al., Nature (1979) 277, 108-114). Alternatively, in the case of the HEF1α promoter/enhancer, the method by Mizushima et al. (Mizushima, S. and Nagata S., Nucleic Acids Res. (1990) 18, 5322) can be used.

When *E. coli* is used, an antibody gene can be expressed by functionally ligating a conventional promoter, a signal sequence for antibody secretion, and the antibody gene to be expressed. Examples of the promoter include a lacZ promoter, araB promoter and such. When a lacZ promoter is used, genes can be expressed according to the method of Ward et al. (Ward, E. S. et al., Nature (1989) 341, 544-546; Ward, E. S. et al., FASEB J. (1992) 6, 2422-2427); and the araB promoter may be used according to the method of Better et al. (Better, M. et al., Science (1988) 240, 1041-1043).

When the antibody is produced into the periplasm of *E. coli*, the pel B signal sequence (Lei, S. P. et al., J. Bacteriol. (1987) 169, 4379-4383) may be used as a signal sequence for antibody secretion. The antibodies produced into the periplasm are isolated, and then used after appropriately refolding the antibody structure (see, for example, WO 96/30394).

As the replication origin, those derived from SV40, polyoma virus, adenovirus, bovine papilloma virus (BPV) and such may be used. In addition, to enhance the gene copy number in a host cell system, the expression vector may comprise the aminoglycoside phosphotransferase (APH) gene, thymidine kinase (TK) gene, *E. coli* xanthine-guanine phosphoribosyltransferase (Ecogpt) gene, dihydrofolate reductase (dhfr) gene, or such as a selection marker.

Any production system may be used to prepare the antibodies for use in the present invention. The production systems for antibody preparation include in vitro and in vivo production systems. In vitro production systems include those using eukaryotic cells or prokaryotic cells.

Production systems using eukaryotic cells include those using animal cells, plant cells, or fungal cells. Such animal cells include (1) Mammalian cells, for example, CHO, COS, myeloma, baby hamster kidney (BHK), HeLa, Vero, and such; (2) amphibian cells, for example, *Xenopus* oocyte; and (3) insect cells, for example, sf9, sf21, Tn5, and such. Known plant cells include cells derived from *Nicotiana tabacum*, which may be cultured as a callus. Known fungal cells include yeasts such as *Saccharomyces* (e.g., *S. cerevisiae*), mold fungi such as *Aspergillus* (e.g., *A. niger*), and such.

Production systems using prokaryotic cells include those using bacterial cells. Known bacterial cells include *E. coli* and *Bacillus subtilis*.

Antibodies can be obtained by using transformation to introduce an antibody gene of interest into these cells, and then culturing the transformed cells in vitro. Cultures are conducted according to known methods. For example, DMEM, MEM, RPMI1640, IMDM may be used as the culture medium, and serum supplements such as FCS may be used in combination. Further, cells introduced with antibody genes may be transferred into the abdominal cavity or such of an animal to produce the antibodies in vivo.

On the other hand, in vivo production systems include those using animals or plants. Production systems using animals include those that use mammals or insects.

Mammals that can be used include goats, pigs, sheep, mice, bovines and such (Vicki Glaser, SPECTRUM Biotechnology Applications, 1993). Further, insects that can be used include silkworms. When using plants, tobacco may be used, for example.

An antibody gene is introduced into these animals or plants, the antibody is produced in the body of the animals or plants, and this antibody is then recovered. For example, an antibody gene can be prepared as a fusion gene by inserting it into the middle of a gene encoding a protein such as goat β casein, which is uniquely produced into milk. DNA fragments comprising the fusion gene, which includes the antibody gene, are injected into goat embryos, and the embryos are introduced into female goats. The desired antibody is obtained from milk produced by the transgenic animals born to the goats that received the embryos, or produced from progenies of these animals. The transgenic goats can be given hormones to increase the volume of milk containing the desired antibody that they produce (Ebert, K. M. et al., Bio/Technology (1994) 12, 699-702).

When silkworms are used, the silkworms are infected with a baculovirus inserted with a desired antibody gene, and the desired antibody is obtained from the body fluids of these silkworm (Maeda, S. et al., Nature (1985) 315, 592-594). Moreover, when tobacco is used, the desired antibody gene is inserted into a plant expression vector (e.g., pMON530) and the vector is introduced into bacteria such as *Agrobacterium tumefaciens*. This bacterium is used to infect tobacco (e.g., *Nicotiana tabacum*) such that desired antibodies can be obtained from the leaves of this tobacco (Julian, K.-C. Ma et al., Eur. J. Immunol. (1994) 24, 131-138).

When producing antibodies using in vitro or in vivo production systems, as described above, DNAs encoding an antibody heavy chain (H chain) and light chain (L chain) may be inserted into separate expression vectors and a host is then co-transformed with the vectors. Alternatively, the DNAs may be inserted into a single expression vector for transforming a host (see International Patent Application Publication No. WO 94/11523).

The antibodies used in the present invention may be antibody fragments or modified products thereof, so long as they can be suitably used in the present invention. For example, antibody fragments include Fab, F(ab')2, Fv, and single chain Fv (scFv), in which the Fvs of the H and L chains are linked via an appropriate linker.

Specifically, the antibody fragments are produced by treating antibodies with enzymes, for example, papain or pepsin, or alternatively, genes encoding these fragments are constructed, introduced into expression vectors, and these are expressed in appropriate host cells (see, for example, Co, M. S. et al., J. Immunol. (1994) 152, 2968-2976; Better, M. & Horwitz, A. H., Methods in Enzymology (1989) 178, 476-496; Plueckthun, A. & Skerra, A., Methods in Enzymology (1989) 178, 497-515; Lamoyi, E., Methods in Enzymology (1989) 121, 652-663; Rousseaux, J. et al., Methods in Enzymology (1989) 121, 663-666; Bird, R. E. et al., TIBTECH (1991) 9, 132-137).

An scFv can be obtained by linking the H-chain V region and the L-chain V region of an antibody. In the scFv, the H-chain V region and the L-chain V region are linked via a linker, preferably via a peptide linker (Huston, J. S. et al., Proc. Natl. Acad. Sci. USA (1988) 85, 5879-5883). The V regions of the H and L chains in an scFv may be derived from any of the antibodies described above. Peptide linkers for linking the V regions include, for example, arbitrary single chain peptides consisting of 12 to 19 amino acid residues.

An scFv-encoding DNA can be obtained by using a DNA encoding an H chain or a V region and a DNA encoding an L chain or a V region of the aforementioned antibodies as templates, using PCR to amplify a DNA portion that encodes the desired amino acid sequence in the template sequence and uses primers that define the termini of the portion, and then further amplifying the amplified DNA portion with a DNA that encodes a peptide linker portion and primer pairs that link both ends of the linker to the H chain and L chain.

Once an scFv-encoding DNA has been obtained, an expression vector comprising the DNA and a host transformed with the vector can be obtained according to conventional methods. In addition, scFv can be obtained according to conventional methods using the host.

As above, these antibody fragments can be produced from the host by obtaining and expressing their genes. Herein, an "antibody" encompasses such antibody fragments.

Antibodies bound to various molecules, such as polyethylene glycol (PEG), may also be used as modified antibodies. Herein, an "antibody" encompasses such modified antibodies. These modified antibodies can be obtained by chemically modifying the obtained antibodies. Such methods are already established in the art.

Antibodies produced and expressed as above can be isolated from the inside or outside of the cells or from the hosts, and then purified to homogeneity. The antibodies for use in the present invention can be isolated and/or purified using affinity chromatography. Columns to be used for the affinity chromatography include, for example, protein A columns and protein G columns. Carriers used for the protein A columns include, for example, HyperD, POROS, Sepharose FF and such. In addition to the above, other methods used for the isolation and/or purification of common proteins may be used, and are not limited in any way.

For example, the antibodies used for the present invention may be isolated and/or purified by appropriately selecting and combining chromatographies in addition to affinity chromatography, filters, ultrafiltration, salting-out, dialysis, and such. Chromatographies include, for example, ion-exchange chromatography, hydrophobic chromatography, gel filtration, and such. These chromatographies can be applied to high performance liquid chromatography (HPLC). Alternatively, reverse phase HPLC may be used.

The concentration of the antibodies obtained as above can be determined by absorbance measurement, ELISA, or such. Specifically, absorbance is determined by appropriately diluting the antibody solution with PBS(−), measuring absorbance at 280 nm, and calculating the concentration (1.35 OD=1 mg/ml). Alternatively, when using ELISA, the measurement can be performed as follows: Specifically, 100 µl of goat anti-human IgG (TAG) diluted to 1 µg/ml with 0.1 M bicarbonate buffer (pH 9.6) is added to a 96-well plate (Nunc) and incubated overnight at 4° C. to immobilize the antibody. After blocking, 100 µl of an appropriately diluted antibody of the present invention or an appropriately diluted sample comprising the antibody, and human IgG (CAPPEL) are added as a standard, and incubated for one hour at room temperature. After washing, 100 µl of 5,000× diluted alkaline phosphatase-labeled anti-human IgG (BIO SOURCE) is added and incubated for one hour at room temperature. After another wash, substrate solution is added and incubated, and the absorbance at 405 nm is measured using a Microplate Reader Model 3550 (Bio-Rad) to calculate the concentration of the antibody of interest.

The IL-6 variants used in the present invention are substances with the activity of binding to an IL-6 receptor and which do not transmit IL-6 biological activity. That is, the IL-6 variants compete with IL-6 to bind to IL-6 receptors, but fail to transmit IL-6 biological activity, and hence the block IL-6-mediated signal transduction.

The IL-6 variants are produced by introducing mutation(s) by substituting amino acid residues in the amino acid sequence of IL-6. The origin of IL-6 used as the base of the IL-6 variants is not limited, but is preferably human IL-6 in consideration of antigenicity and such.

More specifically, amino acid substitutions are performed by predicting the secondary structure of the IL-6 amino acid sequence using known molecular modeling programs (e.g., WHATIF; Vriend et al., J. Mol. Graphics (1990) 8, 52-56), and further assessing the influence of the substituted amino acid residue(s) on the whole molecule. After determining the appropriate amino acid residue to be substituted, commonly performed PCR methods are carried out using a nucleotide sequence encoding a human IL-6 gene as a template, and mutations are introduced to cause amino acids substitutions, and thus genes encoding IL-6 variants are obtained. If needed, this gene is inserted into an appropriate expression vector, and the IL-6 variant can be obtained by applying the aforementioned methods for expression, production, and purification of recombinant antibodies.

Specific examples of the IL-6 variants are disclosed in Brakenhoff et al., J. Biol. Chem. (1994) 269, 86-93, Savino et al., EMBO J. (1994) 13, 1357-1367, WO 96/18648, and WO 96/17869.

The partial peptides of IL-6 and of the IL-6 receptor to be used in the present invention are substances with the activity of binding to the IL-6 receptor and to IL-6, respectively, and which do not transmit IL-6 biological activity. Namely, by binding to and capturing an IL-6 receptor or IL-6, the IL-6 partial peptides or IL-6 receptor partial peptides can specifically inhibit IL-6 from binding to the IL-6 receptor. As a result, the biological activity of IL-6 is not transmitted, and IL-6-mediated signal transduction is blocked.

The partial peptides of IL-6 or IL-6 receptor are peptides that comprise part or all of the amino acid sequence of the region of the IL-6 or IL-6 receptor amino acid sequence that is involved in the binding between the IL-6 and IL-6 receptor. Such peptides usually comprise ten to 80, preferably 20 to 50, more preferably 20 to 40 amino acid residues.

The IL-6 partial peptides or IL-6 receptor partial peptides can be produced according to generally known methods, for example, genetic engineering techniques or peptide synthesis methods, by specifying the region of the IL-6 or IL-6 receptor amino acid sequence that is involved in the binding between the IL-6 and IL-6 receptor, and using a portion or entirety of the amino acid sequence of the specified region.

When preparing an IL-6 partial peptide or IL-6 receptor partial peptide using genetic engineering methods, a DNA sequence encoding the desired peptide is inserted into an expression vector, and then the peptide can be obtained by applying the aforementioned methods for expressing, producing, and purifying recombinant antibodies.

When producing an IL-6 partial peptide or IL-6 receptor partial peptide by using peptide synthesis methods, generally used peptide synthesis methods, for example, solid phase synthesis methods or liquid phase synthesis methods, may be used.

Specifically, the peptides can be synthesized according to the method described in "Continuation of Development of Pharmaceuticals, Vol. 14, Peptide Synthesis (in Japanese) (ed. Haruaki Yajima, 1991, Hirokawa Shoten)". As a solid phase synthesis method, for example, the following method can be employed: the amino acid corresponding to the C terminus of the peptide to be synthesized is bound to a support that is insoluble in organic solvents, then the peptide strand is elongated by alternately repeating (1) the reaction of condensing amino acids, whose α-amino groups and branch chain functional groups are protected with appropriate protecting groups, one at a time in a C- to N-terminal direction; and (2) the reaction of removing the protecting groups from the α-amino groups of the resin-bound amino acids or peptides. Solid phase peptide synthesis is broadly classified into the Boc method and the Fmoc method, depending on the type of protecting groups used.

After synthesizing a protein of interest as above, deprotection reactions are carried out, then the peptide strand is cleaved from its support. For the cleavage reaction of the peptide strand, hydrogen fluoride or trifluoromethane sulfonic acid are generally used for the Boc method, and TFA is generally used for the Fmoc method. In the Boc method, for example, the above-mentioned protected peptide resin is treated with hydrogen fluoride in the presence of anisole. Then, the peptide is recovered by removing the protecting groups and cleaving the peptide from its support. By freeze-drying the recovered peptide, a crude peptide can be obtained. In the Fmoc method, on the other hand, the deprotection reaction and the reaction to cleave the peptide strand from the support can be performed in TFA using a method similar to those described above, for example.

Obtained crude peptides can be separated and/or purified by applying HPLC. Elution may be performed under optimum conditions using a water-acetonitrile solvent system, which is generally used for protein purification. The fractions corresponding to the peaks of the obtained chromatographic profile are collected and freeze-dried. Thus, purified peptide fractions are identified by molecular weight analysis via mass spectrum analysis, amino acid composition analysis, amino acid sequence analysis, or such.

Specific examples of IL-6 partial peptides and IL-6 receptor partial peptides are disclosed in JP-A Hei 2-188600, JP-A Hei 7-324097, JP-A Hei 8-311098, and U.S. Pat. No. 5,210,075.

The antibodies used in the present invention may also be conjugated antibodies that are bound to various molecules, such as polyethylene glycol (PEG), radioactive substances, and toxins. Such conjugated antibodies can be obtained by chemically modifying the obtained antibodies. Methods for modifying antibodies are already established in the art. The "antibodies" of the present invention encompass these conjugated antibodies.

The agents of the present invention for suppressing cytotoxic T cell induction, which comprise IL-6 inhibitors as active ingredients, can be used to suppress post-transplantation rejection.

The present invention also provides agents for suppressing rejection in heart transplantation, which comprise IL-6 inhibitors as active ingredients.

The types of rejection suppressed by the suppressing agents of the present invention are not particularly limited, but are preferably acute rejections, which become problematic in actual transplantation medicine. These rejections are pathological states in which allografts are recognized as foreign antigens due to differences in the major histocompatibility complex (MHC) that determines histocompatibility, and are thus attacked through activation of the recipient's cytotoxic T cells and helper T cells. Rejections are generally developed within three months of transplantation. However, rejections can also be recognized as cell infiltrations into the allograft tissue, three months or more after transplantation.

Herein, "suppressing rejection after transplantation" means improving viability of a transplanted organ by suppressing damage to it.

The types of organ transplantations for which the suppressing agents of the present invention can be used are not particularly limited, and preferred organs for the organ transplantations in the present invention include parenchymal organs, such as hearts, livers, kidneys, pancreas, lungs, and small intestines. The present invention can also be applied to transplantation of tissues such as cardiac valves, vessels, skin, bones, and corneas.

The suppression of a post-transplantation rejection can be confirmed by using a method described in the Examples to determine CTL activity in the subjects following administration of a suppressing agent of the present invention. When a recipient's CTL activity towards a donor's HLA antigen is continuously reduced upon administration of a suppressing agent of the present invention, the agent can be said to suppress transplant failures. When organ viability is improved as a result, the agent can also be said to "suppress transplant failures" in the organ transplantation. The survival of each organ can be assessed by examining whether organ function becomes normal after transplantation.

In the present invention, the activity of IL-6 inhibitors in inhibiting the transduction of IL-6 signals can be evaluated by conventional methods. Specifically, IL-6 is added to cultures of IL-6-dependent human myeloma cell lines (S6B45 and KPMM2), human Lennert T lymphoma cell line KT3, or IL-6-dependent cell line MH60.BSF2; and the $^3$H-thymidine uptake by the IL-6-dependent cells is measured in the presence of an IL-6 inhibitor. Alternatively, IL-6 receptor-expressing U266 cells are cultured, and $^{125}$I-labeled IL-6 and an IL-6 inhibitor are added to the culture at the same time; and then $^{125}$I-labeled IL-6 bound to the IL-6 receptor-expressing cells is quantified. In addition to the IL-6 inhibitor group, a negative control group that does not contain an IL-6 inhibitor is included in the assay system described above. The activity of the IL-6 inhibitor to inhibit IL-6 can be evaluated by comparing the results of both groups.

Subjects to be administered with the suppressing agents of the present invention are mammals. The mammals are preferably humans.

The suppressing agents of the present invention can be administered as pharmaceuticals, and may be administered systemically or locally via oral or parenteral administration. For example, intravenous injections such as drip infusions, intramuscular injections, intraperitoneal injections, subcutaneous injections, suppositories, enemas, oral enteric tablets, or the like can be selected. Appropriate administration methods can be selected depending on a patient's age and symptoms. The effective dose per administration is selected from the range of 0.01 to 100 mg/kg body weight. Alternatively, the dose may be selected from the range of 1 to 1000 mg/patient, preferably from the range of 5 to 50 mg/patient. A preferred dose and administration method are as follows: For example, when an anti-IL-6 receptor antibody is used, the effective dose is an amount such that free antibody is present in the blood. Specifically, a dose of 0.5 to 40 mg/kg body weight/month (four weeks), preferably 1 to 20 mg/kg body weight/month is administered via an intravenous injection such as a drip infusion, subcutaneous injection or such, once to several times a month, for example, twice a week, once a week, once every two weeks, or once every four weeks. The administration schedule may be adjusted by, for example, extending the administration interval of twice a week or once a week to once every two weeks, once every three weeks, or once every four weeks, while monitoring the condition after transplantation and changes in the blood test values.

In the present invention, the suppressing agents may contain pharmaceutically acceptable carriers, such as preservatives and stabilizers. "Pharmaceutically acceptable carriers" refer to materials that can be co-administered with an above-described agent; and may or may not themselves produce the above-described effect of suppressing cytotoxic T cell induction. Alternatively, the carriers may be materials that do not have the effect of suppressing cytotoxic T cell induction, but that produce an additive or synergistic stabilizing effect when used in combination with an IL-6 inhibitor.

Such pharmaceutically acceptable materials include, for example, sterile water, physiological saline, stabilizers, excipients, buffers, preservatives, detergents, chelating agents (EDTA and such), and binders.

In the present invention, detergents include non-ionic detergents, and typical examples of such include sorbitan fatty acid esters such as sorbitan monocaprylate, sorbitan monolaurate, and sorbitan monopalmitate; glycerin fatty acid esters such as glycerin monocaprylate, glycerin monomyristate and glycerin monostearate; polyglycerin fatty acid esters such as decaglyceryl monostearate, decaglyceryl distearate, and decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, and polyoxyethylene sorbitan tristearate; polyoxyethylene sorbit fatty acid esters such as polyoxyethylene sorbit tetrastearate and polyoxyethylene sorbit tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol, polyoxyethylene polyoxypropylene propyl ether, and polyoxyethylene polyoxypropylene cetyl ether; polyoxyethylene alkyl phenyl ethers such as polyoxyethylene nonylphenyl ether; polyoxyethylene hardened castor oils such as polyoxyethylene castor oil and polyoxyethylene hardened castor oil (polyoxyethylene hydrogenated castor oil); polyoxyethylene beeswax derivatives such as polyoxyethylene sorbit beeswax; polyoxyethylene lanolin derivatives such as polyoxyethylene lanolin; and polyoxyethylene fatty acid amides and such with an HLB of six to 18, such as polyoxyethylene stearic acid amide.

Detergents also include anionic detergents, and typical examples of such include, for example, alkylsulfates having an alkyl group with ten to 18 carbon atoms, such as sodium cetylsulfate, sodium laurylsulfate, and sodium oleylsulfate; polyoxyethylene alkyl ether sulfates in which the alkyl group has ten to 18 carbon atoms and the average molar number of added ethylene oxide is 2 to 4, such as sodium polyoxyethylene lauryl sulfate; alkyl sulfosuccinate ester salts having an alkyl group with eight to 18 carbon atoms, such as sodium lauryl sulfosuccinate ester; natural detergents, for example, lecithin; glycerophospholipids; sphingo-phospholipids such as sphingomyelin; and sucrose fatty acid esters in which the fatty acids have 12 to 18 carbon atoms.

One, two or more of the detergents described above can be combined and added to the agents of the present invention. Detergents that are preferably used in the preparations of the present invention include polyoxyethylene sorbitan fatty acid esters, such as polysorbates 20, 40, 60, and 80. Polysorbates 20 and 80 are particularly preferred. Polyoxyethylene polyoxypropylene glycols, such as poloxamer (Pluronic F-68® and such), are also preferred.

The amount of detergent added varies depending on the type of detergent used. When polysorbate 20 or 80 is used, the amount is in general in the range of 0.001 to 100 mg/ml, preferably in the range of 0.003 to 50 mg/ml, more preferably in the range of 0.005 to 2 mg/ml.

In the present invention, buffers include phosphate, citrate buffer, acetic acid, malic acid, tartaric acid, succinic acid, lactic acid, potassium phosphate, gluconic acid, capric acid, deoxycholic acid, salicylic acid, triethanolamine, fumaric acid, and other organic acids; and carbonic acid buffer, Tris buffer, histidine buffer, and imidazole buffer.

Liquid preparations may be formulated by dissolving the agents in aqueous buffers known in the field of liquid preparations. The buffer concentration is in general in the range of 1 to 500 mM, preferably in the range of 5 to 100 mM, more preferably in the range of 10 to 20 mM.

The agents of the present invention may also comprise other low-molecular-weight polypeptides; proteins such as serum albumin, gelatin, and immunoglobulin; amino acids; sugars and carbohydrates such as polysaccharides and monosaccharides, sugar alcohols, and such.

Herein, amino acids include basic amino acids, for example, arginine, lysine, histidine, and ornithine, and inorganic salts of these amino acids (preferably hydrochloride salts, and phosphate salts, namely phosphate amino acids). When free amino acids are used, the pH is adjusted to a preferred value by adding appropriate physiologically acceptable buffering substances, for example, inorganic acids, and in particular hydrochloric acid, phosphoric acid, sulfuric acid, acetic acid, and formic acid, and salts thereof. In this case, the use of phosphate is particularly beneficial because it gives quite stable freeze-dried products. Phosphate is particularly advantageous when preparations do not substantially contain organic acids, such as malic acid, tartaric acid, citric acid, succinic acid, and fumaric acid, or do not contain corresponding anions (malate ion, tartrate ion, citrate ion, succinate ion, fumarate ion, and such). Preferred amino acids are arginine, lysine, histidine, and ornithine. Acidic amino acids can also be used, for example, glutamic acid and aspartic acid, and salts thereof (preferably sodium salts); neutral amino acids, for example, isoleucine, leucine, glycine, serine, threonine, valine, methionine, cysteine, and alanine; and aromatic amino acids, for example, phenylalanine, tyrosine, tryptophan, and its derivative, N-acetyl tryptophan.

Herein, sugars and carbohydrates such as polysaccharides and monosaccharides include, for example, dextran, glucose, fructose, lactose, xylose, mannose, maltose, sucrose, trehalose, and raffinose.

Herein, sugar alcohols include, for example, mannitol, sorbitol, and inositol.

When the agents of the present invention are prepared as aqueous solutions for injection, the agents may be mixed with, for example, physiological saline, and/or isotonic solution containing glucose or other auxiliary agents (such as D-sorbitol, D-mannose, D-mannitol, and sodium chloride). The aqueous solutions may be used in combination with appropriate solubilizing agents such as alcohols (ethanol and such), polyalcohols (propylene glycol, PEG and such), or non-ionic detergents (polysorbate 80 and HCO-50).

The agents may further comprise, if required, diluents, solubilizers, pH adjusters, soothing agents, sulfur-containing reducing agents, antioxidants, and such.

Herein, the sulfur-containing reducing agents include, for example, compounds comprising sulfhydryl groups, such as N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and thioalkanoic acids having one to seven carbon atoms.

Moreover, the antioxidants in the present invention include, for example, erythorbic acid, dibutylhydroxy toluene, butylhydroxy anisole, a-tocopherol, tocopherol acetate, L-ascorbic acid and salts thereof, L-ascorbic acid palmitate, L-ascorbic acid stearate, sodium hydrogen sulfite, sodium sulfite, triamyl galiate, propyl gallate, and chelating agents such as disodium ethylenediamine tetraacetate (EDTA), sodium pyrophosphate, and sodium metaphosphate.

If required, the agents may be encapsulated in microcapsules (microcapsules of hydroxymethylcellulose, gelatin, poly[methylmethacrylic acid] or such) or prepared as colloidal drug delivery systems (liposome, albumin microspheres, microemulsion, nano-particles, nano-capsules, and such) (see "Remington's Pharmaceutical Science 16$^{th}$ edition", Oslo Ed., 1980, and the like). Furthermore, methods for preparing agents as sustained-release agents are also known, and are applicable to the present invention (Langer et al., J. Biomed. Mater. Res. 1981, 15: 167-277; Langer, Chem. Tech. 1982, 12: 98-105; U.S. Pat. No. 3,773,919; European Patent Application No. (EP) 58, 481; Sidman et al., Biopolymers 1983, 22: 547-556; and EP 133,988).

Pharmaceutically acceptable carriers used are appropriately selected from those described above or combined depending on the type of dosage form, but are not limited thereto.

The present invention relates to methods for suppressing rejection after transplantation, which comprise the step of administering IL-6 inhibitors to subjects.

The present invention also relates to methods for suppressing rejection in heart transplantation, which comprise the step of administering IL-6 inhibitors to subjects.

The types of rejections suppressed by the methods of the present invention are not particularly limited, and acute rejections are preferable. The types of organ transplantations for which the suppressing agents of the present invention can be used are not particularly limited. Preferred organs for the organ transplantations in the present invention include parenchymal organs, such as hearts, livers, kidneys, pancreas, lungs, and small intestines. The present invention can also be applied to transplantation of tissues such as cardiac valves, vessels, skin, bones, and corneas.

Herein, the "subject" refers to the organisms or organism body parts to be administered with an IL-6 inhibitor of the present invention. The organisms include animals (for example, human, domestic animal species, and wild animals) but are not particularly limited. The "organism body parts" are not particularly limited.

Herein, "administration" includes oral and parenteral administration. Oral administration includes, for example, administration of oral agents. Such oral agents include, for example, granules, powders, tablets, capsules, solutions, emulsions, and suspensions.

Parenteral administration includes, for example, administration of injections. Such injections include, for example, subcutaneous injections, intramuscular injection s, and intraperitoneal injection. Meanwhile, the effects of the methods of the present invention can be achieved by introducing genes comprising oligonucleotides to be administered to living bodies using gene therapy techniques. Alternatively, the agents of the present invention may be administered locally to intended areas of treatment. For example, the agents can be administered by local injection during surgery, use of catheters, or targeted gene delivery of DNAs encoding peptides of the present invention.

The suppressing agents of the present invention may be administered to subjects prior to organ transplantation, at the time of organ transplantation, or after organ transplantation. Further, the suppressing agents may be administered once or repeatedly.

Alternatively, when administered to an excised or delivered part of an organism, the suppressing agents of the present invention may be "contacted" with the organism part.

In the present invention, "contacting" is performed according to the condition of the organism. Examples include spraying the suppressing agents of the present invention over the organism parts, and adding the suppressing agents of the present invention to crushed organism parts, but are not limited thereto. When the organism part is cultured cells, the above-mentioned "contact" can be achieved by adding the suppressing agents of the present invention to culture medium of these cells, or by introducing DNAs comprising oligonucleotides of the present invention into cells that constitute the organism part.

When conducting the methods of the present invention, the agents of the present invention may be administered as parts of pharmaceutical compositions in combination with at least one known chemotherapeutant. Alternatively, the agents of the present invention may be administered simultaneously with at least one known immunosuppressant. In one embodiment, the known chemotherapeutants and the suppressing agents of the present invention may be administered virtually simultaneously.

The agents for suppressing the induction of cytotoxic T cells of the present invention may be administered to sites of organ transplantation after the organ have been transplanted, or may be administered to targets at the same time as the organ. Alternatively, the agents may be added to the organ in vitro, prior to transplantation.

All prior-art documents cited herein are incorporated herein by reference.

EXAMPLES

Hereinbelow, the present invention will be specifically described with reference to the Examples, but it is not to be construed as being limited thereto.

Example 1

Analysis of the Effect of Anti-IL-6 Receptor Antibody Administration on CTL Activity Against Cells of the Mastocytoma Line P815

First, $3\times10^7$ cells of the mastocytoma line P815 (immunizing cells) were administered intraperitoneally into C57BL/6 mice. After 13 days, spleens were isolated from the mice and the splenic cells (effector cells) were co-cultured with $^{51}$Cr-labeled P815 cells (target cells) at various effector cell/target cell (E/T) ratios to assay the CTL activity against $^{51}$Cr-labeled P815.

CTL activity was assayed by determining the cell lysis rate for each cell sample. Cell lysis rate is expressed as follows:

[(the amount of $^{51}$Cr released in an experiment−the amount of spontaneously released $^{51}$Cr)/(the total amount of released $^{51}$Cr−the amount of spontaneously released $^{51}$Cr)]×100.

Next, 2000 mg and 500 mg of an anti-IL-6 receptor antibody (MR16-1) were intraperitoneally administered four days and one day before isoantigen administration, respectively. Then, four and nine days after isoantigen administration, 500 mg of the antibody was administered. CTL activity was determined by the methods described above. Meanwhile, under the same treatment conditions, control mice were injected with rat IgG as a control antibody, instead of the anti-IL-6 receptor antibody. CTL activity was determined by the same method as described above.

Figure 2:
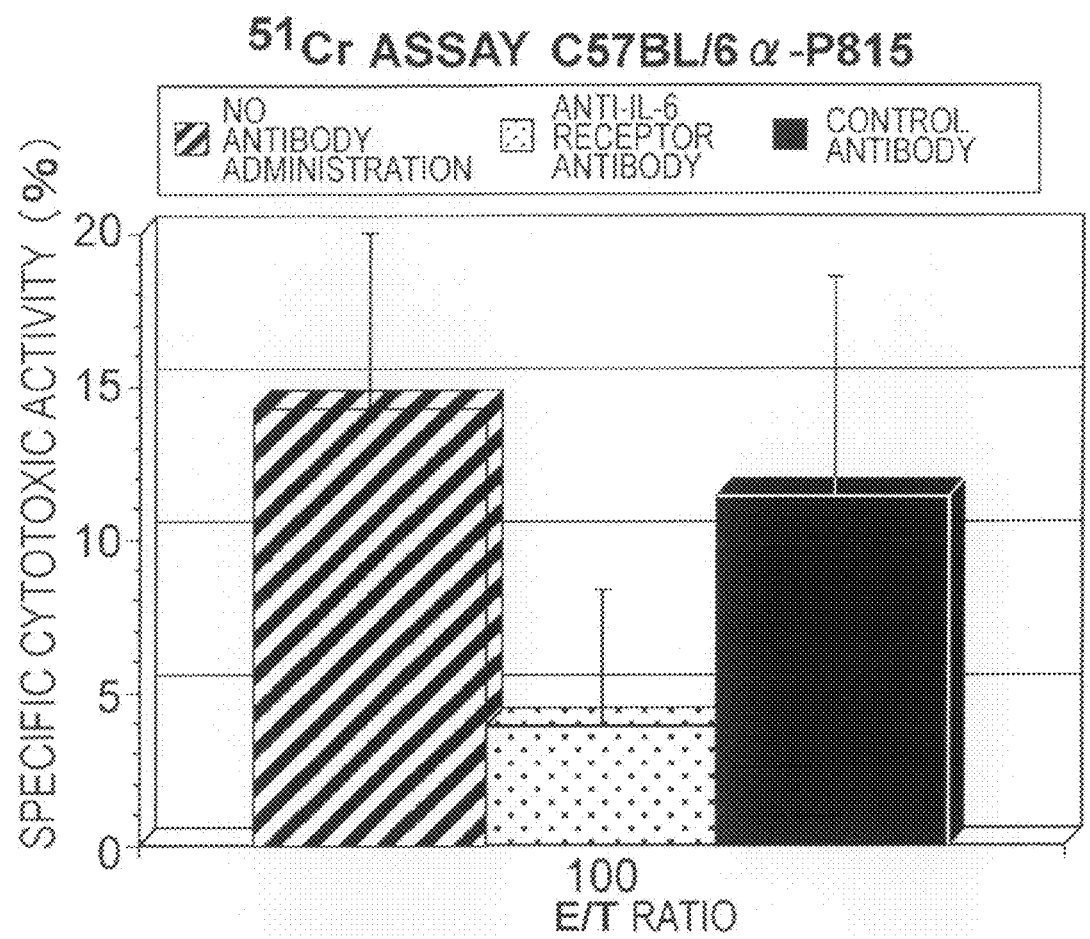
FIG. 2 shows the specific cytotoxic activity (CTL activity) when the E/T ratio is 100 in mice not treated with an antibody, mice treated with an anti-IL-6 receptor antibody, and mice treated with a control antibody, where each was administered with cells of mastocytoma line P815.

The results obtained in the assays described above showed that CTL activity against the alloantigen (mastocytoma line P815) was statistically significantly reduced in mice treated with the anti-IL-6 receptor antibody as compared to mice not treated with any antibodies and mice treated with the control antibody (FIGS. 1 and 2). ($p<0.01$) When P815 cells were introduced into IL-6-deficient C57BL/6 mice, the level of in-vivo CTL induction was found to be significantly reduced (data not shown).

Example 2

Analysis of the Effect of Anti-IL-6 Receptor Antibody Administration on CTL Activity Against Cells of the EL4 Lymphoma Cell Line By the same procedure as described above, $3\times10^7$ cells of the EL4 lymphoma cell line (immunizing cells) were administered intraperitoneally into BALB/c mice. After 13 days, spleens were isolated from the mice and the splenic cells (effector cells) were co-cultured with $^{51}$Cr-labeled EL4 cells (target cells) at various effector cell/target cell (E/T) ratios. CTL activity against $^{51}$Cr-labeled EL4 was assayed using the same method as described in Example 1. Next, using the same procedure as described in Example 1, 2000 mg and 500 mg of the anti-IL-6 receptor antibody were intraperitoneally administered four days and one day before isoantigen administration, respectively. Then, four and nine days after isoantigen administration, 500 mg of the antibody was administered. CTL activity was determined by the method described above. In addition, under the same treatment conditions, control mice were injected with rat IgG as a control antibody, instead of the anti-IL-6 receptor antibody. CTL activity was determined using the methods described above.

Figure 3:
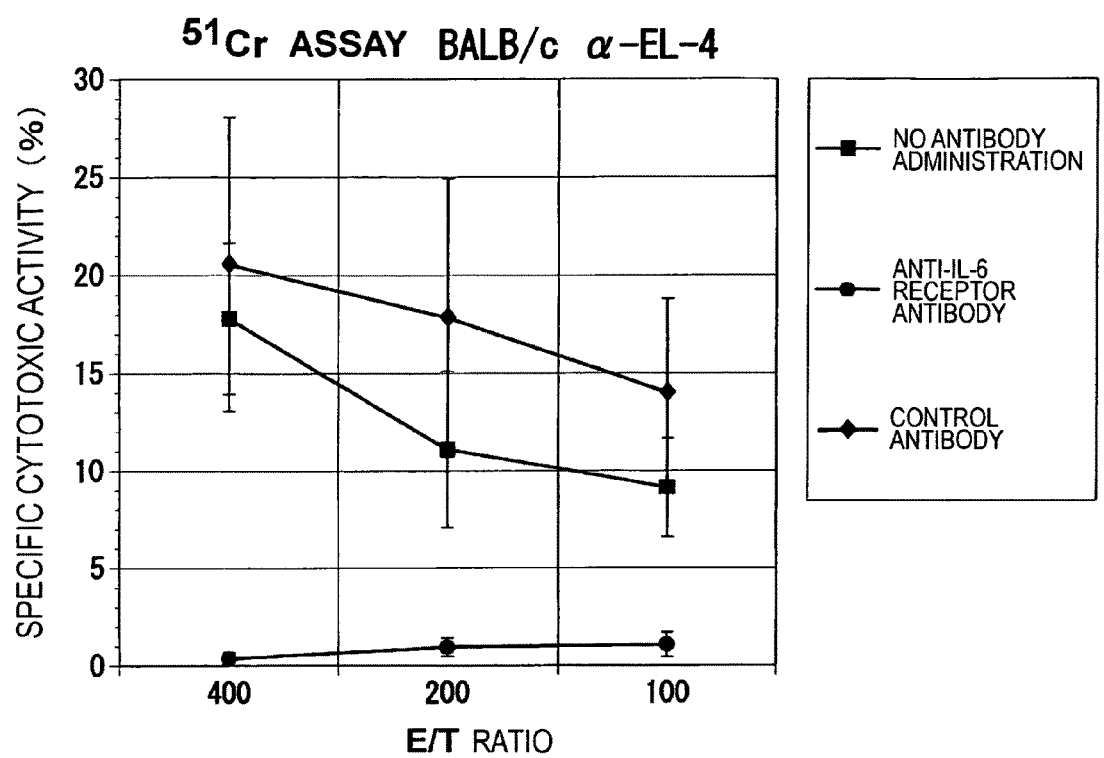
FIG. 3 shows the specific cytotoxic activity (CTL activity) at each E/T ratio in mice not treated with an antibody, mice treated with an anti-IL-6 receptor antibody, and mice treated with a control antibody, where each was administered with EL4 lymphoma cells.
Figure 4:
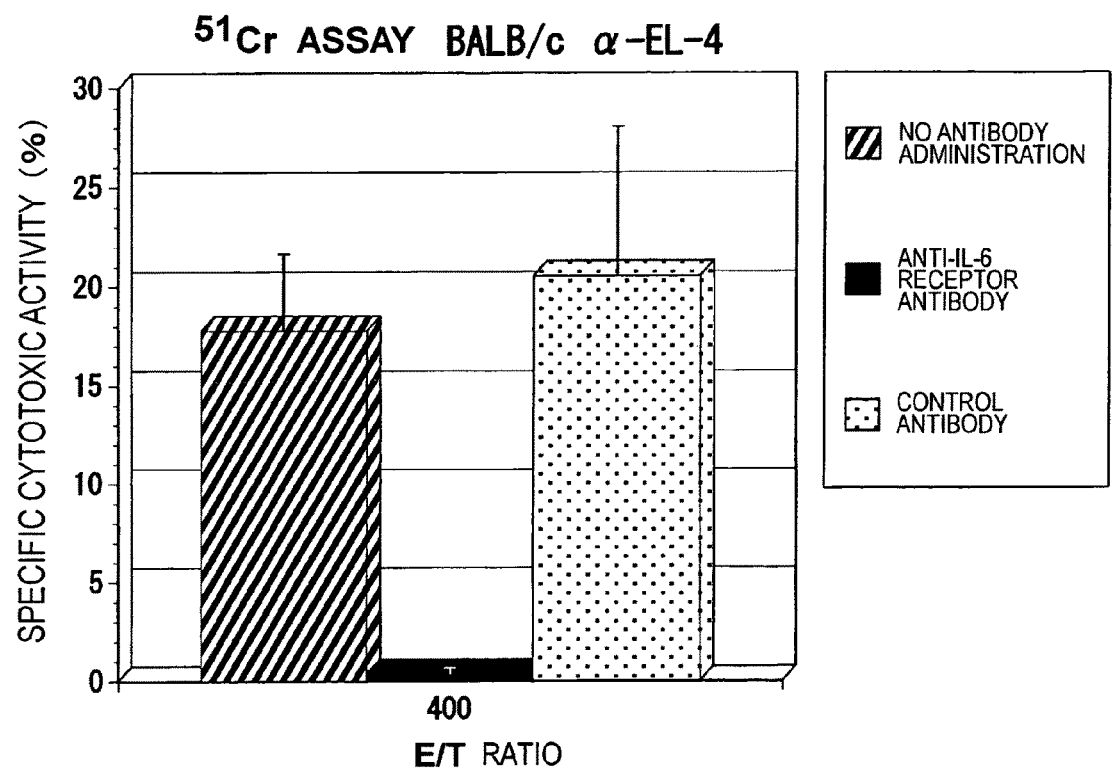
FIG. 4 shows the specific cytotoxic activity (CTL activity) when the E/T ratio is 400 in mice not treated with an antibody, mice treated with an anti-IL-6 receptor antibody, and mice treated with a control antibody, where each was administered with EL4 lymphoma cells.

The results obtained in the assays described above showed that CTL activity against the alloantigen (EL4 lymphoma line) was statistically significantly reduced in mice treated with the anti-IL-6 receptor antibody, as compared with mice not treated with any antibodies and mice treated with the control antibody (FIGS. 3 and 4). ($p<0.01$)

The results described above showed that the anti-IL-6 receptor antibody had functions to suppress cytotoxic T cell induction.

Example 3

Assessment of the Effect of Anti-IL-6 Receptor Antibody Administration in a Mouse Model for Acute Heart Transplant Rejection The effect of administering an anti-IL-6 receptor antibody (MR16-1) on acute rejection after transplantation was assessed using a mouse model for heart transplantation. The mice used in the experiments were purchased from Japan SLC Inc. and bred at the Division of Laboratory Animal Research, Department of Life Science, Research Center for Human and Environmental Sciences, Shinshu University, according to the center's animal experiment protocol. A mouse model for heterotopic heart transplantation using BALB/c mouse donors and C57BL/6 mouse recipients, which are allogenic, was prepared by microsurgery using the procedure described below. The donors and recipients used were four- to eight-week-old male mice.

Both donor and recipient mice were anesthetized by intraperitoneally injecting pentobarbital sodium (Nenbutal(R)) at a dose of 70 mg/kg. The heart to be transplanted was isolated after ligating vessels other than ascending aorta and pulmonary artery to be used for anastomosis. The isolated heart graft was preserved in cold physiological saline containing 7.5% heparin on ice. The recipient was laparotomized in the midline and the intestines were flipped over to expose the abdominal aorta and inferior vena cava. After blood flow was stopped using microclips for microvessels, an about 1-mm incision was created on each surface for anastomotic sites. The aorta and the pulmonary artery of the transplanted heart were anastomosed to the abdominal aorta and the inferior vena cava of the recipient, respectively, by continuous suture using 10-0 nylon suture. The microclips were unfastened gradually to resume the blood flow. The transplanted heart was confirmed to resume beating. After confirming hemorrhage arrest, the abdominal wall and the skin were sutured to close the abdomen.

Each surgery took about 45 minutes. The success rate was 95% or greater.

The treated group were intraperitoneally injected with the anti-IL-6 receptor antibody at a dose of 2 mg/mouse/administration immediately, three days, and six days after transplantation. Beating of the transplanted heart was confirmed every day by abdominal palpation. When the heart completely stopped beating, the heart was concluded to have been rejected. At that time, the recipient was anesthetized and laparotomized to confirm by visual inspection that the heart had stopped beating. Time until rejection was defined as the survival period of the cardiac allograft. The periods were compared with each other.

Figure 5:
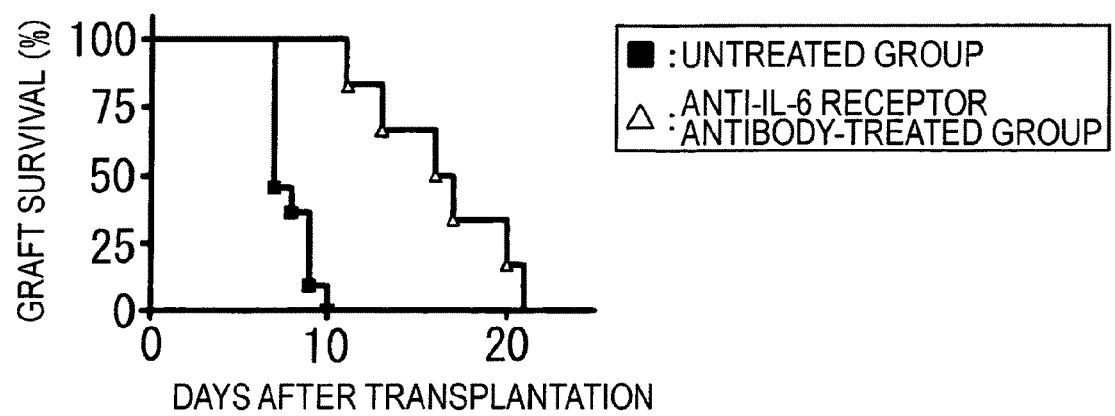
FIG. 5 shows the viability of transplanted hearts in the group treated with an anti-IL-6 receptor antibody and the untreated group, in the mouse model for heart transplantation.

The results showed that administration of the anti-IL-6 receptor antibody suppressed acute rejection of cardiac allografts and statistically significantly prolonged the allograft survival (FIG. 5). ($p=0.0001$)

Untreated group: 7, 7, 7, 7, 7, 7, 8, 9, 9, 9, and 10 (days). (11 cases, Median survival time: seven days).

Anti-IL-6 receptor antibody-treated group: 11, 13, 16, 17, 20, and 21 (days). (six cases, Median survival time: 16.5 days).

Furthermore, five days after transplantation, the cardiac allografts were isolated from the recipients for histological examination.

Figure 6:
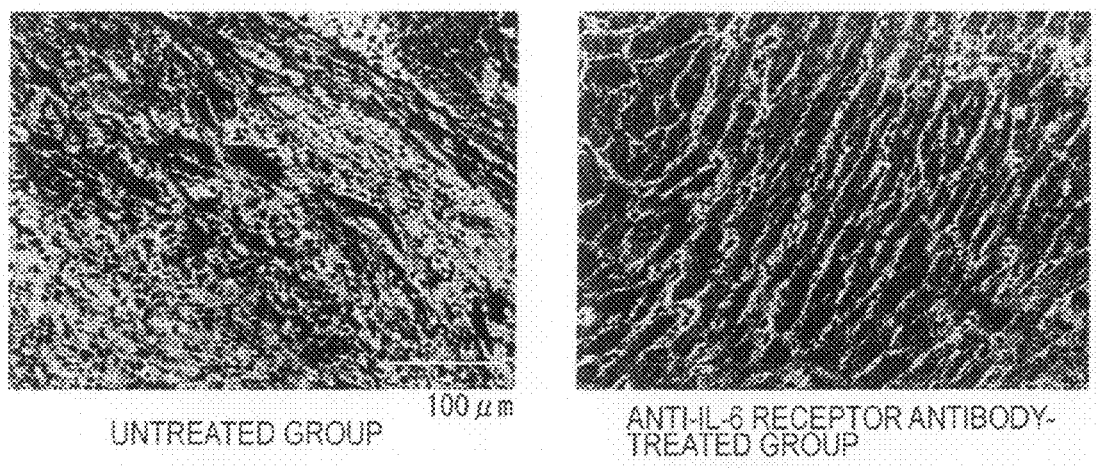
FIG. 6 is photographs showing histopathological images of transplanted hearts five days after transplantation, for the group treated with an anti-IL-6 receptor antibody and the untreated group, in the mouse model for heart transplantation.

Pathological tissue sections were prepared from frozen tissue samples of the cardiac allografts five days after transplantation, and these were stained with hematoxylin-eosin. Diffuse infiltration of inflammatory cells and myocardial necrosis were found in the untreated group. In the anti-IL-6 receptor antibody-treated group, the infiltration of inflammatory cells was mild and cardiomyocytes were relatively preserved (FIG. 6).

Figure 7:
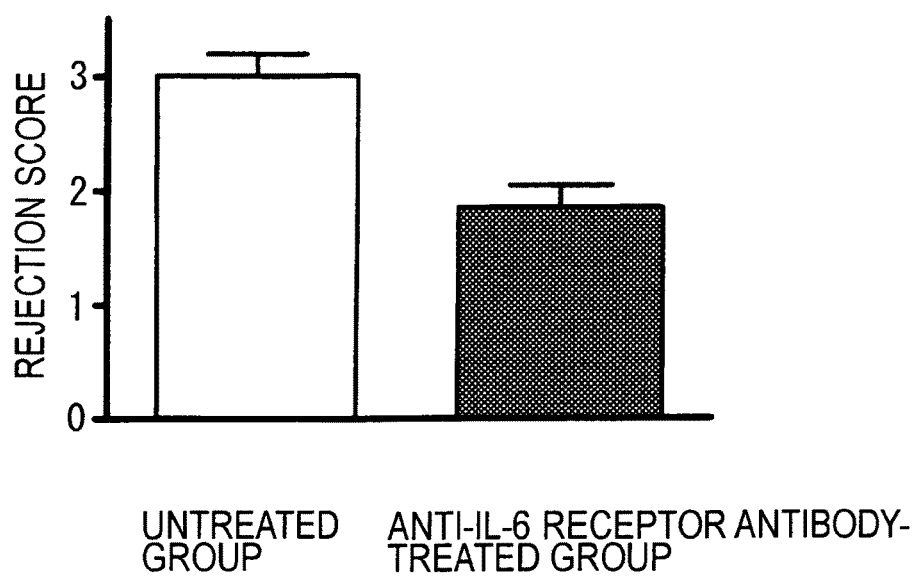
FIG. 7 shows the results of comparing rejection scores for transplanted hearts five days after transplantation between the group treated with an anti-IL-6 receptor antibody and the untreated group, in the mouse model for heart transplantation.

The results of histological analysis were scored according to the five step criteria of "0: no rejection" to "4: severe rejection" (Rodriguez, E. R. The pathology of heart transplant biopsy specimens: revisiting the 1990 ISHLT working formulation. J Heart Lung Transplant. (2003) 22, 3-15% Billingham, M. E. et al., A working formulation for the standardization of nomenclature in the diagnosis of heart and lung rejection: Heart Rejection Study Group. The International Society for Heart Transplantation. J Heart Transplant. (1990) 9, 587-93). When the rejection score for the anti-IL-6 receptor antibody-treated group was compared with that of the untreated group, significant suppression was revealed in the treated group (FIG. 7). (p=0.0006)

The above results showed that administration of an anti-IL-6 receptor antibody to recipients suppressed acute rejection of cardiac allografts and statistically significantly prolonged the allograft survival in the mouse model for heart transplantation.

INDUSTRIAL APPLICABILITY

The present invention demonstrated that cytotoxic T cells induction could be suppressed by administering an anti-IL-6 receptor antibody.

The invention also demonstrated that immunorejections after transplantation could be suppressed by administering the anti-IL-6 receptor antibody.

The invention claimed is:

1. A method for suppressing acute rejection of a heart transplant in a subject, the method comprising administering to the subject an interleukin-6 (IL-6) biological activity inhibitor that is an antibody that recognizes an IL-6 receptor, thereby suppressing acute rejection of the heart transplant in the subject.

2. The method of claim 1, wherein the antibody is a monoclonal antibody.

3. The method of claim 1, wherein the antibody recognizes a human IL-6 receptor.

4. The method of claim 1, wherein the antibody is a recombinant antibody.

5. The method of claim 1, wherein the antibody is a chimeric antibody, humanized antibody, or human antibody.

6. The method of claim 1, wherein the antibody is a scFv.

7. The method of claim 1, wherein the inhibitor is administered to the subject repeatedly.

8. The method of claim 1, wherein the inhibitor is administered prior to transplantation of the heart into the subject.

9. The method of claim 1, wherein the inhibitor is administered at the time of transplantation of the heart into the subject.

10. The method of claim 1, wherein the inhibitor is administered after transplantation of the heart into the subject.

11. The method of claim 1, wherein the inhibitor is administered immediately after transplantation of the heart into the subject.

12. The method of claim 1, wherein the inhibitor is administered three days after transplantation of the heart into the subject.

13. The method of claim 1, wherein the inhibitor is administered six days after transplantation of the heart into the subject.

14. The method of claim 1, wherein the method further comprises confirming that acute rejection of the transplanted heart is suppressed.

15. The method of claim 1, wherein the method further comprises assaying cytotoxic T cell activity in the subject following administration of the inhibitor.

16. The method of claim 1, wherein the subject is a human subject.

17. The method of claim 1, wherein the antibody is administered in a dose of 0.01 to 100 mg/kg per administration.

18. The method of claim 1, wherein the antibody is administered in a dose of 1 to 1000 mg/patient.

19. The method of claim 1, wherein the antibody is administered in a dose of 0.5 to 40 mg/kg body weight/month.

20. The method of claim 1, wherein the inhibitor is administered to the subject once.

* * * * *